United States Patent
Lang et al.

(10) Patent No.: US 6,730,034 B1
(45) Date of Patent: *May 4, 2004

(54) ULTRASONIC METHODS AND DEVICES FOR MEASUREMENT OF BODY FAT

(76) Inventors: Philipp Lang, 225 Lincoln Way #206, San Francisco, CA (US) 94122; John D. Mendlein, 680 Neptune Ave., Encinitas, CA (US) 92024

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/097,772

(22) Filed: Jun. 15, 1998

(51) Int. Cl.[7] .............................. A61B 8/00
(52) U.S. Cl. ..................................... 600/449
(58) Field of Search ................. 600/437, 443, 600/445, 446, 447, 459, 462, 454, 455, 301, 409

(56) References Cited

U.S. PATENT DOCUMENTS

| | | | |
|---|---|---|---|
| 4,198,989 A | | 4/1980 | Hawke et al. |
| D255,938 S | | 7/1980 | Hawke et al. |
| 4,321,752 A | | 3/1982 | Kaufman |
| 4,388,831 A | | 6/1983 | Sherman |
| 4,413,629 A | * | 11/1983 | Durley, III .................. 600/437 |
| 4,483,075 A | | 11/1984 | Kundin |
| 4,785,817 A | * | 11/1988 | Stouffer ...................... 600/443 |
| 5,170,790 A | * | 12/1992 | Lacoste et al. ............. 600/455 |
| 5,216,817 A | | 6/1993 | Misevich et al. |
| 5,235,988 A | | 8/1993 | Johnson et al. |
| 5,316,003 A | | 5/1994 | Stouffer |
| 5,553,618 A | * | 9/1996 | Suzuki et al. ................ 600/407 |
| 5,598,845 A | * | 2/1997 | Chandraratna et al. ..... 600/459 |
| 5,640,960 A | * | 6/1997 | Jones et al. .................. 600/453 |
| 5,865,733 A | * | 2/1999 | Malinouskas et al. ....... 600/300 |
| 5,941,825 A | | 8/1999 | Lang et al. |

OTHER PUBLICATIONS

Abe, T., et al., Appl Human Sci, vol. 14 (3), pp. 133–139, 1995.

Davidoff, A., et al., J Clin Ultrasound, vol. 22 (4), pp. 263–267, 1994.

Gerecke, W. B., Anesthesiology, vol. 28 (1), pp. 213–214, 1967.

Khati, N. J., et al., Radiographics, vol. 182 (2), pp. 413–431, 1998.

Kohrt, W. M., et al., Med Sci Sports Exerc, vol. 24 (7), pp. 832–837, 1992.

Kuhns, L. R., et al., Am J Roentgenol, vol. 131 (1), pp. 115–117, 1978.

Maruschak, G. F., Anesth Analg, vol. 52 (1), pp. 29–30, 1973.

Rosenberg J. C., et al., Obstet Gynecol, vol. 85(1), pp. 132–134, 1995.

Seidell, J. C., et al., Eur J Clin Invest, vol. 18 (3), pp. 243–249, 1988.

Takahashi, M., et al., Horm Metab Res, vol. 28 (12), pp. 751–752, 1996.

* cited by examiner

Primary Examiner—Ali M. Imam
(74) Attorney, Agent, or Firm—Hale and Dorr LLP

(57) ABSTRACT

The invention provides for methods, compositions, and devices for measuring adipose tissue and lean tissue using ultrasonic methods, compositions and devices, particularly methods, compositions and devices that facilitate placement of ultrasonic probe(s) using external anatomic landmarks such as the umbilicus, and methods, compositions, and devices that improve the reproducibility of ultrasonic measurements of object layer thickness.

26 Claims, 8 Drawing Sheets

ULTRASONIC METHODS AND DEVICES FOR MEASUREMENT OF BODY FAT

TECHNICAL FIELD

The invention relates to the measurement of adipose tissue and lean tissue using ultrasonic methods, compositions and devices, particularly methods, compositions and devices that facilitate placement of ultrasonic probe(s) using external anatomic landmarks, such as the umbilicus, and improve the reproducibility of ultrasonic measurements of object layer thickness.

BACKGROUND

Objects often include layers of different compositions that are difficult to measure directly and accurately. In many cases, the object's interior can not be accessed to allow for direct measurement. It may be impractical to intrude the object's interior or, if even using non-invasive techniques, it may be difficult to position the probe for accurate measurements.

For measurements of biological specimens, the thickness of underlying layers are particularly inconvenient to measure. Many such measurements are preferably taken in vivo, which makes invasive techniques impractical. If non-invasive techniques are used, they are often susceptible to operator errors and can be quite costly, as in the case of expensive medical diagnostic equipment.

In the case of body adipose tissue layers, measurements with skin calipers and water immersion tanks can be used to assess body adipose tissue. Such techniques, however, have a number of drawbacks.

Skinfold calipers use the principle that the amount of subcutaneous adipose tissue correlates to percent body adipose tissue (American College of Sports Medicine, ACSM's guidelines for exercise testing and prescription, 53–63 (1995)). With a skinfold caliper measurement, after the skin is pinched by an operator without inducing pain to the subject, the thickness of the skinfold is measured with the caliper. Caliper measurements of skinfold thickness have been used with various equations developed to predict body density and percent body adipose tissue (American College of Sports Medicine, ACSM's guidelines for exercise testing and prescription, 53–63 (1995)). Most of these equations, however, are sex-specific or only apply to certain populations. Other equations to estimate body density and percent body adipose tissue have been developed using regression models that can take into account data from larger population based studies (Jackson, A. S., Pollock, M. L., Br J Nutr, 1978: 497–504 (1978)).

Even with these improvements, however, skinfold calipers are subject to several serious sources of errors. First, skinfold caliper measurements are heavily operator dependent. The force used to pull back the skin by the operator and the location of the measurement site may vary significantly between different operators, or the same operator, resulting in poor reproducibility of measurements. Second, even though skinfold caliper measurements are based on the assumption that subcutaneous adipose tissue thickness correlates to percent body adipose tissue, skinfold calipers cannot measure the thickness of subcutaneous adipose tissue directly. Skinfold caliper measurements, instead, provide an estimate of subcutaneous adipose tissue thickness which, in turn, is then used to estimate percent body adipose tissue. Thus, two approximations are used to estimate percent body adipose tissue. Third, skinfold caliper measurements may overestimate subcutaneous adipose tissue thickness. When the skinfold is pulled back for the measurement, adipose tissue from adjacent sites can be pulled toward the measurement site causing an artificial increase in the amount of subcutaneous adipose tissue present in the selected body region. This problem is exaggerated in subjects with very elastic soft-tissue. Fourth, the inaccuracies associated with skinfold caliper measurements have lead to the use of equations requiring measurements of 3 body sites, 4 body sites, and even 7 body sites (American College of Sports Medicine, ACSM's guidelines for exercise testing and prescription, 53–63 (1995)). However, even with these adjustments, the inherent inaccuracies of skinfold caliper measurements, most importantly the inability to measure subcutaneous adipose tissue thickness directly, cannot be completely compensated.

Hydrostatic weighing is commonly considered the gold standard for determining body density and estimating percent body adipose tissue. Hydrostatic weighing relies on Archimedes' principle. A body submerged in water is buoyed by a counterforce equal to the weight of the water that it displaced. Bone and muscle tissue are denser than water, while adipose tissue is less dense. Therefore, a person with low percent body adipose tissue will have higher body density and weighs more in water than a person with higher percent body adipose tissue and the same air weight. Conversely, a person with higher percent body adipose tissue for the same air weight will weigh less in water.

Although hydrostatic weighing is considered the gold standard for body adipose tissue determinations, it is subject to several sources of error. First, hydrostatic weighing requires estimation of pulmonary residual volume, which may vary significantly between individuals. Although pulmonary residual volume can be measured using pulmonary function tests, this adds extra time and expense to the procedure, which could decrease patient compliance. Second, hydrostatic weighing does not account for the variability in bone density known to exist between different individuals and races (American College of Sports Medicine, ACSM's guidelines for exercise testing and prescription, 53–63 (1995)). In patients with high bone density, hydrostatic weighing will underestimate percent body adipose tissue. Conversely, in osteoporotic patients, hydrostatic weighing may seriously overestimate percent body adipose tissue. Third, hydrostatic weighing requires large and expensive displacement chambers, and complete patient immersion in water. The technical requirements and the expense of hydrostatic weighing limit its use in frequent longitudinal measurements of percent body adipose tissue that are desirable in ambulatory patients undergoing a nutritional regimen or exercise induced adipose tissue reduction. Fourth, submersion of the head underwater may be difficult or anxiety provoking for some individuals.

Ultrasonic examination has been used by the inventors of the present invention for assessing subcutaneous fat and muscle layer thickness (see PCT application PCT/US97/18993). While the previous inventions addressed and improved probe interrogation and positioning, reproducibility of ultrasonic measurements of subcutaneous fat and muscle layer thickness could be further improved by reducing other types of operator induced errors in ultrasonic probe positioning.

For example, to measure a fat layer, the probe may be placed in the abdominal region, the supraclavicular region, the suprailiac region, or the thigh region. These regions are, however, often difficult to reproducibly locate and frequently include anatomical areas stretching over several square centimeters of potential interrogation sites, which leads to significant variability in ultrasonic probe placement. This can result in inaccurate repeat measurements if probe placement is not generally maintained over the original interrogation site.

The variability in probe placement and in resultant ultrasonic measurements is typically even greater when measurements are not performed by a trained operator or when self-measurements are obtained. This variability in probe position and alignment decreases the reproducibility of the ultrasonic measurements which is of particular importance when repeat measurements are obtained at different time intervals as a means of detecting a longitudinal change in physiologic parameters measured by ultrasound. Repeat measurements of subcutaneous fat thickness are, for example, critical for monitoring the effects of a diet. Repeat measurements of muscle layer thickness are important for monitoring the effects of a physical exercise program.

Consequently, the present inventors have recognized the need for methods and devices for improving the accuracy and reproducibility of ultrasonic probe positioning and ultrasonic measurements. Methods and devices are provided herein that aid in positioning of ultrasonic probes.

The present invention describes for the first time the use of methods and devices for positioning an ultrasonic probe reproducibly on a subject's body surface with use of external reference landmarks. Such methods or devices help to improve the reproducibility of ultrasonic measurements, such as measurements of the thickness of a tissue layer such as the subcutaneous fat layer or the muscle tissue layer.

SUMMARY

The invention provides for an ultrasonic system for interrogation of an antomical region, such as an abdomen or an appendage. The primary use of such a system is to interrogate an adipose or muscle tissue layer in an abdomen or an appendage. Typically, the ultrasonic system includes an ultrasonic probe for handheld interrogation of a human abdomen, and an an umbilicus positioning unit for positioning the ultrasonic probe in an umbilicus of the human abdomen. Usually, the system includes a computational unit, which can be designed to calculate layer thickness (e.g. an adipose layer) or, if desired, body fat. Preferably, the computational unit can process signals in A scan mode or may be designed to only process signals in A scan mode.

One embodiment of the umbilicus positioning unit typically comprises a bulb to fit in a human umbilicus while permitting the ultrasonic probe to be in acoustic contact with the human abdomen. The bulb can be secured at a predetermined dimension from the ultrasonic probe. Alternatively, the umbilicus positioning unit can comprise a positioning member on a face of the ultrasonic probe to position the ultrasonic probe directly over the umbilicus. Typically, the ultrasonic transducers are oriented to project a beam through the tissue to assess layer thickness or some other property of the tissue. The umbilicus positioning unit can include a pressure sensor to detect, directly or indirectly, pressure on a face of the probe. The umbilicus positioning unit and the computational unit can be encased in a housing. Preferably, such housing is handheld. The umbilicus positioning unit usually reduces variations in ultrasonic measurement of the thickness of human abdomen layer(s) by providing a consistent reference site for interrogation. The umbilicus positioning unit may include a plastic member shaped to snugly fit in an umbilicus. Umbilicus positioning units described herein can be used to make anatomically compatible ultrasonic probes.

The umbilicus positioning unit is typically designed with a positioning member that engages an umbilicus while permitting acoustic contact of the ultrasonic probe with the human abdomen or interrogation sites at other locations. The umbilicus positioning unit, for instance, can include an arm that connects the positioning member to the ultrasonic probe. The arm may be of a predetermined distance, as well as extendable or retractable or both. The arm permits the ultrasonic probe to interrogate the human abdomen or other anatomical regions at a predetermined distance from an umbilicus.

The umbilicus positioning unit is often designed with a tip that engages, or forms a portion of, a housing that holds the ultrasonic probe. The unit may be constructed to permit the ultrasonic probe to generally transmit through the tip. Other embodiments may have substantially no diagnostically relevant transmission through the tip, such as for adjacent interrogation. The tip is typically between about 1 cm and about 4 cm in length. It can have a selected diameter sized to in fit in an umbilicus of choice.

The invention also provides for a handheld, ultrasonic probe. A handheld, ultrasonic probe may include at least a first ultrasonic source to transmit an ultrasonic pulse to a human abdomen, at least a first ultrasonic detector to detect ultrasonic waves from the human abdomen, and an umbilicus positioning unit to position the ultrasonic source and detector. The umbilicus positioning unit and the probe are sized for inclusion in a handheld structure for interrogation of the human abdomen or other site. Often the umbilicus positioning unit will comprise an integral part of the housing of the device. The ultrasonic source and detector can be solely transmitter and receiver transducers, such as for BUA or SOS, or included in the same transducer, such as for A scan. The handheld device may optionally contain a computational unit. Typically, the probe and the computational unit are encased in a housing and the entire unit is handheld. Preferably, the computational unit calculates layer thickness in the object and the probe, and the computational unit and a display are adapted for A-scan.

The invention also provides for an umbilicus positioning unit that can be attached to an ultrasonic probe. Many existing and future probes can benefit from the invention by the attachment of an umbilicus positioning unit. Typically, an attachable umbilicus positioning unit comprises a polymeric material that is shaped or molded to the form of the probe's exterior. The umbilicus positioning unit can be designed with a friction fit member sized for an ultrasonic probe. The umbilicus positioning unit may slidably and snugly engage the handheld ultrasonic probe. The umbilicus positioning unit may be designed to permit 1) positioning of the ultrasonic probe when interrogating an abdomen and 2) removal of the umbilicus positioning unit from the handheld ultrasonic probe to allow interrogation of other anatomical regions without the umbilicus positioning unit attached to the handheld ultrasonic probe.

The invention also provides for an ultrasonic probe with an anatomical reference member, such as an anatomically compatible ultrasonic probe holder. The anatomical reference member can be used by an operator to permit interrogation in a controllable fashion with respect to a selected anatomical site that may or may not be the site of interrogation. Typically, a first end of the anatomical reference member is positioned with respect to an anatomical site and either a second end or first portion of the anatomical reference member engages or contains an ultrasonic transducer. Usually, the first end engages, holds, or otherwise fits a desired anatomical region. Usually, a handheld, ultrasonic probe includes at least a first ultrasonic source to transmit an ultrasonic pulse to a tissue, at least a first ultrasonic detector to detect ultrasonic waves from the tissue, and an anatomical reference member for reducing probe misplacement and increasing reproducibility of probe positioning with respect to a pre-selected anatomical region for which the anatomical reference member is adapted. The first ultrasonic source and detector, and the anatomical reference member are usually sized for inclusion in a handheld structure for interrogation of the tissue. The probe can include a computational unit. The ultrasonic probe can also include a plurality of separate transducers, such as at least three ultrasonic sources and at least three ultrasonic detectors.

The anatomical reference member can be of a single length or extendable or retractable or both. The anatomical reference member for instance can include an extendable and retractable member to controllably change the distance between the anatomical reference member and the first ultrasonic source and detector or multiple transducers. The anatomical reference member can be designed to allow the first ultrasonic source to transmit generally through the umbilicus positioning unit for diagnostic transmission. Alternatively, the first ultrasonic source may not transmit generally through the anatomical reference member. The anatomical reference member can include a securing member of a substantially flat surface. The securing member stabilizes the probe on the interrogation surface, such as on a surface of an abdomen.

The first ultrasonic source and detector may be disposed in the anatomical reference member. For instance, the anatomical reference member can comprise a ring disposed with respect to the first ultrasonic source and detector at a predetermined distance. The ring is of sufficient diameter to permit a finger to enter the ring and touch a desired anatomical region. The ring permits the operator to controllably position the anatomical reference member and the first ultrasonic source and detector with respect to the desired anatomical region. Alternatively, the anatomical reference member may comprise a convex surface disposed with respect to the first ultrasonic source and detector at a predetermined distance. The convex surface is of sufficient diameter to engage a desired anatomical region. The convex surface permits the operator to controllably position the anatomical reference member and the first ultrasonic source and detector with respect to the desired anatomical region. The convex surface permits interrogation of a site, such as a wrist.

The invention also provides for a kit for monitoring and enhancing adipose tissue loss comprising devices described herein and various health treatments.

DETAILED DESCRIPTION OF THE INVENTION

Abbreviations and Definitions

Figure 1:
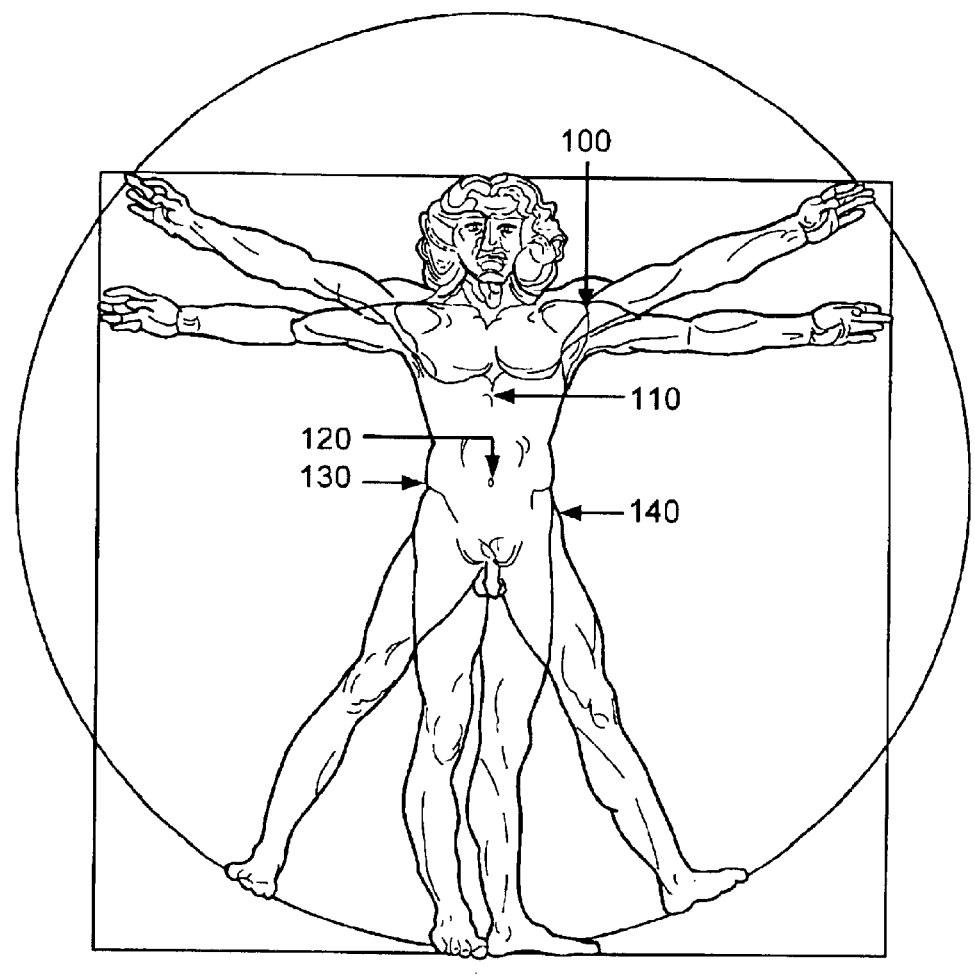
FIG. 1 shows selected, exemplary external landmarks that can be used for ultrasonic monitoring of adipose tissue layer thickness, total body fat, and percent body fat in a human in need of such monitoring. Exemplary external landmarks for ultrasonic interrogation include but are not limited to the acromioclavicular joint 100, the xiphoid process 110, the umbilicus 120, the superior aspect of the iliac crest 130, the anterior superior iliac spine 140. The exemplary regions illustrated in FIG. 1 can be used alone or in combination, as described herein.

Abbreviations include broadband ultrasonic attenuation (BUA) and speed of sound (SOS).

Acoustic communication refers to the passage of ultrasonic waves between two points in a predetermined manner. Usually, this is accomplished by selecting a desired pathway between the two points that permits the passage of ultrasonic waves either directly or indirectly. Direct passage of ultrasonic waves would occur, for instance, when an ultrasonic crystal is directly disposed to (usually touching) an acoustic coupling material, such as a composite. Indirect passage of ultrasonic waves would occur, for instance, when an ultrasonic crystal is located at a predetermined distance from an acoustic coupling material or when a number of acoustic coupling materials, often heterogenous materials, form two or more layers.

Acoustic coupler refers to a connection or plurality of connections between an ultrasonic crystal and a substance that reflects or passes ultrasonic pulses and is not part of the device or object being interrogated. The acoustic coupler will permit passage of ultrasonic waves. It is desirable for such couplers to minimize attenuation of ultrasonic pulses or signals and to minimize changes in the physical properties of an ultrasonic wave, such as wave amplitude, frequency, shape and wavelength. Typically, an ultrasonic coupler will either comprise a gel or other substantially soft material, such as a pliable polymer matrix, that can transmit ultrasonic pulses. Alternatively, an ultrasonic coupler can be a substantially solid material, such as a polymer matrix, that can transmit ultrasonic pulses. An ultrasonic coupler is usually selected based on its acoustic impedance match between the object being interrogated and the ultrasonic crystal(s). If a reflective surface is desired, for instance as a spatial marker, a larger impedance difference is selected compared to situations where it is advantageous to minimize a reflective surface to avoid a sharp reflective surface.

Acoustic coupling material is a material that passes ultrasonic waves, usually from a probe to a subject or tissue to be interrogated. It is usually not a living material and is most often a polymer or gel or acoustic coupler.

Acoustic mirror refers to a device that can reflect an ultrasonic wave and redirect the ultrasonic wave in a predetermined manner. If the original ultrasonic waves are transmitted at an angle $\alpha$, which is measured relative to the surface of the plane of the acoustic mirror, the reflected ultrasonic waves can be oriented at an angle $\alpha'=180°-\alpha$ relative to the plane of the acoustic mirror. An acoustic mirror(s) can be used in an ultrasonic system to vary the transmission angle.

Anatomical region refers to a site on the surface of the skin, tumor, organ or other definable biomass that can be identified by an anatomical feature(s) or location. Anatomical region can include the biomass underlying the surface. Usually, such a region will be definable according to standard medical reference methodology, such as that found in Williams et al., Gray's Anatomy, 1980.

Anatomically compatible refers to the shape of a tissue interrogation probe, device or holder where the external form, contour or surface of the same follows, or corresponds to, the contour of a body surface in a desired interrogated region. An anatomically compatible ultrasonic probe or an anatomically compatible ultrasonic probe holder has a shape adapted to achieve acoustic coupling or an anatomic fit, or both, between the probe or probe holder and the external body surface in the interrogated region, preferably a recognized contour(s) of an external landmark(s). For example, an anatomically compatible ultrasonic probe for interrogation in the region subjacent to the umbilicus can have a cone shape or a cylindrical shape with a cone shaped tip to fit into an umbilicus cavity. An anatomically compatible ultrasonic probe or ultrasonic probe holder for interrogation in the region of the thigh can have concave shape or a semicircular shape.

A-scan refers to an ultrasonic technique where an ultrasonic source transmits an ultrasonic wave into an object, such as a patient's body, and the amplitude of the returning echoes (signals) are recorded as a function of time. Structures that lie along the direction of propagation are interrogated. As echoes return from interfaces within the object or tissue, the transducer crystal produces a voltage that is proportional to the echo intensity. The sequence of signal acquisition and processing of A-scan data in a modern ultrasonic instrument usually occurs in six major steps:

Detection of the echo (signal) occurs via mechanical deformation of the piezoelectric crystal and is converted to an electric signal having a small voltage.

Preamplification of the electronic signal from the crystal, into a more useful range of voltages is usually necessary to ensure appropriate signal processing.

Time Gain Compensation compensates for the attenuation of the ultrasonic signal with time, which arises from travel distance. Time gain compensation may be user-adjustable and may be changed to meet the needs of the specific application. Usually, the ideal time gain compensation curve corrects the signal for the depth of the reflective boundary. Time gain compensation works by increasing the amplification factor of the signal as a function of time after the ultrasonic pulse has been emitted. Thus, reflective boundaries having equal abilities to reflect ultrasonic waves will have equal ultrasonic signals, regardless of the depth of the boundary.

Compression of the time compensated signal can be accomplished using logarithmic amplification to reduce the large dynamic range (range of smallest to largest signals) of the echo amplitudes. Small signals are made larger and large signals are made smaller. This step provides a convenient scale for display of the amplitude variations on the limited gray scale range of a monitor.

Rectification, demodulation and envelope detection of the high frequency electronic signal permits the sampling and digitization of the echo amplitude free of variations induced by the sinusoidal nature of the waveform.

Rejection level adjustment sets the threshold of signal amplitudes that are permitted to enter a data storage, processing or display system. Rejection of lower signal amplitudes reduces noise levels from scattered ultrasonic signals.

BUA means broadband ultrasonic attenuation and when measured a BUA value is expressed as dB/MHz. Note that actual attenuation of broadband ultrasonic waves increases as soft tissue thickness increases, while BUA values (dB/MHz) decrease as soft tissue thickness increases. This distinction is often not recognized in the literature, which leads to misleading or potentially misleading conclusions about the effect of soft tissue on actual attenuation of broadband ultrasonic waves and BUA values.

B-scan refers to an ultrasonic technique where the amplitude of the detected returning echo is recorded as a function of the transmission time, the relative location of the detector in the probe and the signal amplitude. This is often represented by the brightness of a visual element, such as a pixel, in a two-dimensional image. The position of the pixel along the y-axis represents the depth, i.e. half the time for the echo to return to the transducer (for one half of the distance traveled). The position along the x-axis represents the location of the returning echoes relative to the long axis of the transducer, i.e. the location of the pixel either in a superoinferior or mediolateral direction or a combination of both. The display of multiple adjacent scan lines creates a composite two-dimensional image that portrays the general contour of internal organs.

Chip refers to any current and future electronic hardware device that can be used in a computational unit or can be used as an aid in controlling the components of an ultrasonic unit including: 1) timing and synchronizing trigger pulses and subsequent transmission of ultrasonic waves, 2) measuring and analyzing incoming ultrasonic signals, 3) comparing data to predetermined standards and data cut-offs (e.g. electronic filtering), 4) performing multiple other simple and complex calculations, and 5) data storage. Typically, a chip is silicon-based, micro-electronic circuit.

Computational unit refers to any current or future hardware, software (e.g. computer program), chip or other device used for calculations, data storage, or for providing instructions now developed or developed in the future or combination thereof. The computational unit may be used for controlling the ultrasonic generator or source, for defining or varying the firing rate and pulse repetition rate (as well as other parameters related to the ultrasonic generator or source), for measuring a reflected signal, for image reconstruction in B-scan mode and for filtering and thresholding of the ultrasonic signal. Other applications of the computational unit to the methods and devices described herein will be recognized by those skilled in the art. The computational unit may be used for any other application related to this technology that may be facilitated with use of computer software or hardware. The computational unit may comprise a computer program product with instructions to control the ultrasonic system or a database product. Such computer program products or database product may be stored in storage devices, such as hard drives, floppy discs, electronic storage devices or any other storage device capable of reliable storage and retrieval of information (including electronic signals).

Crystal refers to the material used in the ultrasonic transducer to transmit ultrasonic waves and includes any current and future material used for this purpose. Crystals typically consist of lead zirconate titanate, barium lead titanate, lead metaniobate, lithium sulfate and polyvinylidene fluoride or a combination thereof. A crystal is typically a piezoelectric material, but any material that will contract and expand when an external voltage is applied can be used, if such a material can generate ultrasonic waves described herein and known in the art. Crystals emit ultrasonic waves because the rapid mechanical contraction and expansion of the material moves the medium to generate ultrasonic waves. Conversely, when incoming ultrasonic waves deform the crystal, a current is induced in the material. The material then emits an electrical discharge that can be measured and, ultimately, with B-scan technology, can be used to reconstruct an image. Crystals or combinations of crystals with dipoles that approximate the acoustic impedance of human tissue are preferred, so as to reduce the impedance mismatch at the tissue/probe interface.

Detector refers to any structure capable of measuring an ultrasonic wave or pulse, currently known or developed in the future. Crystals containing dipoles are typically used to measure ultrasonic waves. Crystals, such as piezoelectric crystals, shift in dipole orientation in response to an applied electric current. If the applied electric current fluctuates, the crystals vibrate to cause an ultrasonic wave in a medium. Conversely, crystals vibrate in response to an ultrasonic wave that mechanically deforms the crystals, which changes dipole alignment within the crystal. This, in turn, changes the charge distribution to generate an electric current across a crystal's surface. Electrodes connected to electronic circuitry sense a potential difference across the crystal in relation to the incident mechanical pressure. A transducer can be a detector.

Echogenicity refers to the brightness of a tissue in an ultrasonic image relative to the adjacent tissues, typically on a B-scan image. Echogenicity is dependent on the amount of ultrasonic waves reflected by the tissue. Certain tissues are more echogenic than other tissues. Fatty tissue, for example, is more echogenic than muscle tissue. For identical imaging parameters, fatty tissue will thus appear brighter than muscle tissue. Consequently, image brightness can be used to identify different tissues.

External landmarks are anatomical features can be identified visually as a protuberance or indentation in the outer contour of a human body or that can be identified using manual palpation and compression of the skin, subcutaneous tissues, or muscle or combination thereof. An external landmark can be composed of soft-tissue, e.g. skin and subcutaneous fat in the umbilicus, or of dense tissue, e.g. cartilage or bone. External reference landmarks include, but are not limited to, the umbilicus, the acromioclavicular joint, the scapular spine, the xiphoid process, the superior aspect of the iliac crest, the anterior superior iliac spine, the posterior superior iliac spine, and the greater trochanter.

Frame time, when used in the context of positioning an ultrasonic source, refers to the time that is required to move an ultrasonic source using a mechanical motor or other current and future devices. Frame time typically ranges from 10 ms to 2,000 ms.

Handheld device refers to a device such as a probe, that can be grasped by a human hand without substantial interference of another structure. Preferably, handheld devices are wireless (e.g. not electronically connected to an ultrasound system). Examples of wireless devices include (1) a handheld ultrasound system designed to control transmission, process signals, and provide information to an external entity, such as an operator or computer, via a display or other means, (2) a handheld ultrasound system including all or some of the features of (1) as well as a data storage unit (e.g. a chip) to store data for data transmission (e.g. post interrogation), and (3) a handheld ultrasound system that operates completely independently of another system, such as an ultrasound system with a signal processing and a display unit.

Linear array refers to a transducer design where the crystals are arranged in a linear fashion along one or more axes. Crystals can be fired in sequential, as well as non-sequential and simultaneous firing patterns or a combination thereof. With sequential firing, each crystal can produce an ultrasonic beam and receive a returning echo for data collection. The number of crystals in one array usually determines the number of lines of sight for each recording. With segmental firing, a group or segment of crystals can be activated simultaneously resulting in a deeper near field and a less divergent far field compared with sequential activation. A segmental linear array produces, however, a smaller number of lines of sight when compared to a sequential linear array with the same number of crystals.

Plane refers to the surface of a cross-sectional area of tissue interrogated by an ultrasonic probe. In ultrasonic measurements, the portion of the tissue included in the measurement or image is more accurately referred to as a volume. The x-dimension of this volume reflects the length of the tissue plane, i.e. the length of imaged tissue. The x-dimension typically varies between 1 and 10 cm or more. The y-dimension of this volume reflects tissue depth from the plane, e.g. the distance from the skin surface to a reflection point in the tissue. Interrogation of the y-dimension (or depth of the interrogation) depends, among other things, on the type of transducer, the type of tissue, and the frequency with which the ultrasonic beam is transmitted. With higher frequencies, tissue penetration decreases and the maximum depth from the tissue plane will decrease. The y-dimension typically varies between 1 and 30 cm. The z-dimension corresponds to the width of the plane that is interrogated. It typically varies between 1 and 15–20 mm. It is understood that such dimensions are in reference to ultrasonic signals and interrogation.

Paraumbilical region refers to an anatomical location adjacent to the umbilicus. A paraumbilical region can be located superior, inferior, medial, or lateral to the umbilicus. The distance between the umbilicus and a paraumbilical region does typically not exceed 10 cm, more typically 5 cm.

Transmission angle refers to the angle of an ultrasonic beam that intersects the object or tissue plane. The transmission angle is normally measured with respect to the object or tissue plane. The object or tissue plane has a reference angle of zero degrees. For example, as the transmission angle increases toward 90 degrees relative to the tissue plane, the ultrasonic beam approaches an orthogonal position relative to the tissue plane. Preferably, ultrasonic measurements are performed when the ultrasonic beam is orthogonal to the plane of the tissue. It is also preferable, in some embodiments of the invention, to vary the transmission angle in a predetermined and controllable manner in order to interrogate anatomical region as a function of a pre-selected transmission angle(s). For example, transmission angle can be varied by changing the angle of a transducer with respect to the object to be interrogated.

Transmission frequency refers to the frequency of the ultrasonic wave that is being transmitted from the ultrasonic source. Transmission frequency typically ranges between 0.2 MHz and 25MHz. Higher frequencies usually provide higher spatial resolution. Tissue penetration decreases with higher frequencies. Lower transmission frequencies are generally characterized by lower spatial resolution with improved tissue penetration.

Ultrasonic probe or ultrasonic transducer refers to a device that is capable of transmitting and/or receiving ultrasonic signals or waves. An ultrasonic probe or transducer can contain a single or multiple ultrasonic sources. If multiple ultrasonic sources are used in an ultrasonic probe or transducer, they can be arranged in a linear pattern thereby forming a linear array, in a curvilinear pattern thereby forming a curvilinear array, in an annular pattern thereby forming an annular array, or any other current and future pattern.

Ultrasonic probe holder refers to a device that holds an ultrasonic probe or transducer. The ultrasonic probe or transducer can be permanently attached to the ultrasonic probe holder or it can be detachable from the ultrasonic probe holder. Ultrasonic probe holders can help to improve the reproducibility of ultrasonic measurements. Ultrasonic probe holders can be anatomically compatible for selected anatomic regions.

Ultrasonic pulse refers to any ultrasonic wave transmitted by an ultrasonic source. Typically, the pulse will have a predetermined amplitude, frequency, and wave shape. Ultrasonic pulses may range in frequency between 20 kHz and 20 Mhz or higher. Ultrasonic pulses may consist of sine waves with single frequency or varying frequencies, as well as single amplitudes and varying amplitudes. In addition to sine waves, square waves or any other wave pattern may be employed. Square waves may be obtained by adding single-frequency sine waves to other sine waves. The summation of waves can then result in a square wave pattern.

Ultrasonic signal refers to any ultrasonic wave measured by an ultrasonic detector after it has been reflected from the interface of an object or tissue. Ultrasonic signals may range in frequency between 20 kHz and 20 Mhz or higher.

Ultrasonic source refers to any structure capable of generating an ultrasonic wave or pulse, currently known or developed in the future. Crystals containing dipoles are typically used to generate an ultrasonic wave above 20 khz. Crystals, such as piezoelectric crystals, that vibrate in response to an electric current applied to the crystal can be used as an ultrasonic source. In some ultrasonic generators, multiple ultrasonic sources may be arranged in a linear fashion. This arrangement of ultrasonic sources is also referred to as a linear array. With linear arrays, ultrasonic sources are typically fired sequentially, although simultaneous firing of groups of adjacent ultrasonic sources or other firing patterns of individual or groups of ultrasonic sources with various time delays can be achieved as described herein or developed in the art. The time delay between individual or group firings can be used to vary the depth of the beam in an object.

Ultrasonic wave refers to either an ultrasonic signal or pulse.

2.0 Introduction

The present invention recognizes for the first time that ultrasonic tissue interrogation for measurement of tissue layer thickness, such as adipose or lean tissue thickness in a human, can be improved by using an anatomically compatible ultrasonic probe or an anatomically compatible ultrasonic probe holder adapted for a particular anatomical region, as described herein for the embodiments of the invention. Such designs are configured for use on the integument and non-mucosal membranes. Previously, it was not recognized that ultrasonic measurements of layer thickness of an object or a tissue could be improved using new probe designs to increase positioning reproducibility, as described herein. Nor was it previously recognized that use of an anatomically compatible ultrasonic probe or an anatomically compatible ultrasonic probe holder adapted for one or more external landmarks on the body surface of a subject, such as the umbilicus, can be used to improve reproducibility of ultrasonic probe positioning and resultant measurements of object or tissue layer thickness, as described herein.

By way of introduction, and not limitation of the various embodiments of the invention, the invention includes at least six general aspects:

1) an anatomically compatible ultrasonic probe or an anatomically compatible ultrasonic probe holder with a shape adapted to achieve an acoustic coupling or an anatomic fit, or both, of the ultrasonic probe or the ultrasonic probe holder onto an external anatomic landmark on the body surface and for measuring tissue layer thickness in a subject, particularly adipose tissue or lean tissue layer thickness, 2) an anatomically compatible ultrasonic probe with a shape adapted to achieve an acoustic coupling or an anatomical fit, or both, between the probe and the inside of an umbilicus, 3) an anatomically compatible ultrasonic probe holder with a shape adapted to achieve a fit between the probe holder and the inside of an umbilicus, 4) an ultrasonic method of measuring tissue layer thickness in a subject, particularly adipose tissue or lean tissue layer thickness, by using predefined ultrasonic transmission angles which can be equal or less than 90 degrees relative to the interrogated tissue plane and in reference to a predefined anatomical site, 5) an ultrasonic method of measuring tissue layer thickness in a subject, particularly adipose tissue or lean tissue layer thickness, by using ultrasonic probes and holders of the invention, 6) an ultrasonic system or hand-held ultrasonic system that includes an anatomically compatible ultrasonic probe or an anatomically compatible ultrasonic probe holder for tissue measurement, a computational unit to control and process ultrasonic wave generation and detection, and a display to communicate tissue measurements to the operator.

These aspects of the invention, as well as others described herein, can be achieved using the methods and devices described herein. To gain a full appreciation of the scope of the invention, it will be further recognized that various aspects of the invention can be combined to make desirable embodiments of the invention. For example, the invention includes a self-measurement, hand-held system and includes characteristics of aspects (2), (4), and (6). Such combinations result in particularly useful and robust embodiments of the invention.

3.0 Anatomically Compatible Ultrasonic Probes

Ultrasound can be used for measurements of tissue properties, such as adipose tissue thickness, at a variety of anatomical regions of adipose deposition. Measurements of adipose deposition can be performed for example in the chest, abdomen, axilla, triceps, biceps, subscapular, suprailiac, thigh, and calf region. However, the boundaries and locations of these anatomic regions are often poorly defined, vary significantly between different subjects and can be mis-identified or not reproducibly identified by an operator. Additionally, the boundaries and locations of these anatomic regions can vary significantly within the same subject during the course of a diet, a nutritional regimen, or an exercise program. The poor definition of the anatomic boundaries of these ultrasonic measurement sites and the resultant variability in ultrasonic probe positioning lead to poor reproducibility of ultrasonic measurements of object layer thickness, e.g. thickness of the adipose tissue layer or a lean tissue layer such as muscle tissue. This, in turn, makes measurement of longitudinal changes in object layer thickness, e.g. measurement of adipose tissue layer thickness over time, such as during a diet or a nutritional regimen, difficult, if not impossible in some subjects.

For example, a reproducibility error of ultrasonic measurements of object layer thickness of 20% in a subject with a true anatomic adipose layer thickness of 5 cm in the abdominal region can result in over- or underestimation of the adipose tissue layer thickness by 1 cm. An absolute measurement error of 1 cm in adipose tissue layer thickness can correspond to a difference in body weight of several kilograms depending on the subject's size and body habitus, as well as a marked difference in percent body adipose tissue. Such over- or underestimation of adipose tissue layer thickness may explain some of the discrepancies that have been observed in the past between ultrasonic estimates of total body fat based on measurements of adipose tissue thickness and results achieved with hydrostatic weighing. The limited reproducibility of ultrasonic measurements of object layer thickness, such as adipose or lean tissue layer thickness is further aggravated when the subject performs self-measurements. The reproducibility error of ultrasonic measurements of object layer thickness is one of the reasons why ultrasound has not found widespread application for measuring adipose tissue thickness for monitoring the effects of a diet or a nutritional regimen.

The present invention provides for methods and devices that improve the reproducibility of ultrasonic measurements of object layer thickness, such as adipose or lean tissue in a human or a mammal. In one embodiment of the invention, an anatomically compatible ultrasonic probe is used for ultrasonic measurement of object layer thickness, e.g. thickness of adipose tissue or muscle tissue in a human. Such probes include anatomical reference members as described herein. The anatomically compatible ultrasonic probe is shaped so that its external form follows the contour of the body surface in the interrogated region. For example, in the region of the thigh or the anterior superior iliac spine and iliac crest, the anatomically compatible ultrasonic probe can have a concave or a semicircular shape that follows the contour of the thigh in mediolateral direction. In the thigh region, the transducer surface of the ultrasonic probe can be 5 cm, more preferably 10 cm long in the mediolateral direction and 1–3 cm, more preferably 3–6 cm wide in superoinferior direction. A width of 3–6 cm in the superoinferior direction is preferable since it helps stabilize the probe against the thigh thereby decreasing potential errors in probe angulation. In the region of the anterior superior iliac spine and the iliac crest, the transducer surface can be 5 cm, more preferably 10 cm long in the mediolateral direction and 2–4 cm, more preferably 4–8 cm wide in superoinferior direction. A width of 4–8 cm in the superoinferior direction is preferable since it helps stabilize the transducer surface against the abdominal wall in the region of the anterior superior iliac spine and the iliac crest thereby decreasing potential errors in probe angulation.

The degree of concavity or convexity can be varied to adjust for inter-individual variations in body surface shape. Variation of the concavity or or convexity can be, for example, achieved with use of one or more hinges deployed along the length of the probe or with use of a deformable plastic material or metal.

In another embodiment, the length of the anatomical reference member of the probe can be variable, for example with use of an extendable member. Such extendable members can be composed of multiple interlocking or telescoping segments. Each segment may fit inside of the other.

Alternatively, different preformed anatomical reference members, either integrated or attachable to the probe, with different length, width, and concavity or convexity or both can be made available for the different anatomic locations and the operator can choose the one that provides a good anatomic fit, good stabilization of the probe against the skin in order to decrease errors in probe angulation, and good anatomic coupling.

The surface of the ultrasonic probe can be flat and not formed to follow the contour of the body surface in the interrogated region. Instead, an anatomically compatible solid acoustic coupling medium that follows the contour of the body surface in the interrogated region can be interposed between the skin and the surface of the ultrasonic probe. Such an anatomically compatible solid acoustic coupling medium is preferably composed of current and future materials that transmit ultrasonic waves without substantially attenuating the ultrasonic beam, such as epoxy resins or epoxy resins with enclosed aluminum powder. Typically, these solid acoustic coupling media are not deformable. In this case, a set of differently shaped solid acoustic coupling media each with fixed size and shape can be used and the patient or the physician can select the one that provides a good fit, good anatomically compatible probe positioning, and good acoustic coupling for a given anatomic region in each individual patient. However, in some embodiments a solid acoustic coupling material composed of a deformable plastic or metal may be preferred. In this case, the operator will form the solid acoustic coupling medium so that its shape will follow the body surface over the interrogated region and so that it can be adjusted for individual subjects.

Use of an anatomically compatible ultrasonic probe can aid in achieving more reproducible positioning of the ultrasonic probe over the same anatomic region when repeated measurements are performed. Use of an anatomically compatible ultrasonic probe can also help to avoid positioning of the probe at angles other than 90 degrees relative to the body surface or the interrogated tissue. Ultrasonic probe positioning at angles other than 90 degrees relative to the body surface or the interrogated tissue can lead to overestimation of object layer thickness (see also PCT patent application PCT/US97/18993).

Another embodiment of the invention, includes an anatomically compatible ultrasonic probe with a shape that follows the contour of an external landmark. The external landmark can be identified by the operator visually as a protuberance or indentation in the outer contour of the subject's body or it can be identified by the operator using manual palpation and compression of the skin, subcutaneous tissues, or muscle or a combination thereof. An anatomical reference member can be included in an anatomically compatible ultrasonic probe, as described further herein, and designed to fit or "mate" with the desired anatomical site or external reference landmark. In some instances the ultrasonic probe itself may be the anatomical reference member. The external landmark can be composed of soft-tissue, e.g. skin and subcutaneous fat in the umbilicus, or of dense tissue, e.g. cartilage or bone. External reference landmarks include, but are not limited to, (see also FIG. 1):

Acromioclavicular joint (100),
Xiphoid process (110),
Umbilicus (120),
Superior aspect of the iliac crest (130),
Anterior superior iliac spine (140),
Scapular spine,
Posterior superior iliac spine and
Greater trochanter.

Other external landmarks include the knee joint space, the patella, the anterior tibia, the medial and lateral malleolus, the metatarsophalangeal joints, the interphalangeal joints of the foot, the olecranon, the distal radius, the distal ulna, the carpometacarpal joints, the metacarphophalangeal joints, and the interphalangeal joints of the hand.

In many applications, an anatomically compatible ultrasonic probe is placed directly over the external landmark for measurement of the subjacent object layer thickness, e.g. adipose tissue or lean tissue layer thickness. In some embodiments, the anatomically compatible ultrasonic probe is placed adjacent to the external landmark for measurement of the adjacent object layer thicknesses, e.g. adipose tissue or lean tissue layer thickness. In this case, an anatomically compatible ultrasonic probe holder or anatomical reference member is preferable (see Section 4.0). Positioning of the ultrasonic probe adjacent to the external landmark can be achieved with use of an ultrasonic probe holder or anatomical reference member. Use of an external landmark as a reference for positioning of an ultrasonic probe helps to improve the reproducibility of ultrasonic probe positioning and helps interrogating the same tissue area and volume when repeated ultrasonic measurements are performed. Use of an anatomically compatible ultrasonic probe or probe holder that follows the contour of the anatomic landmark thereby improves the reproducibility of ultrasonic measurements of object layer thickness, e.g. adipose tissue thickness or lean tissue thickness.

Figure 2A:
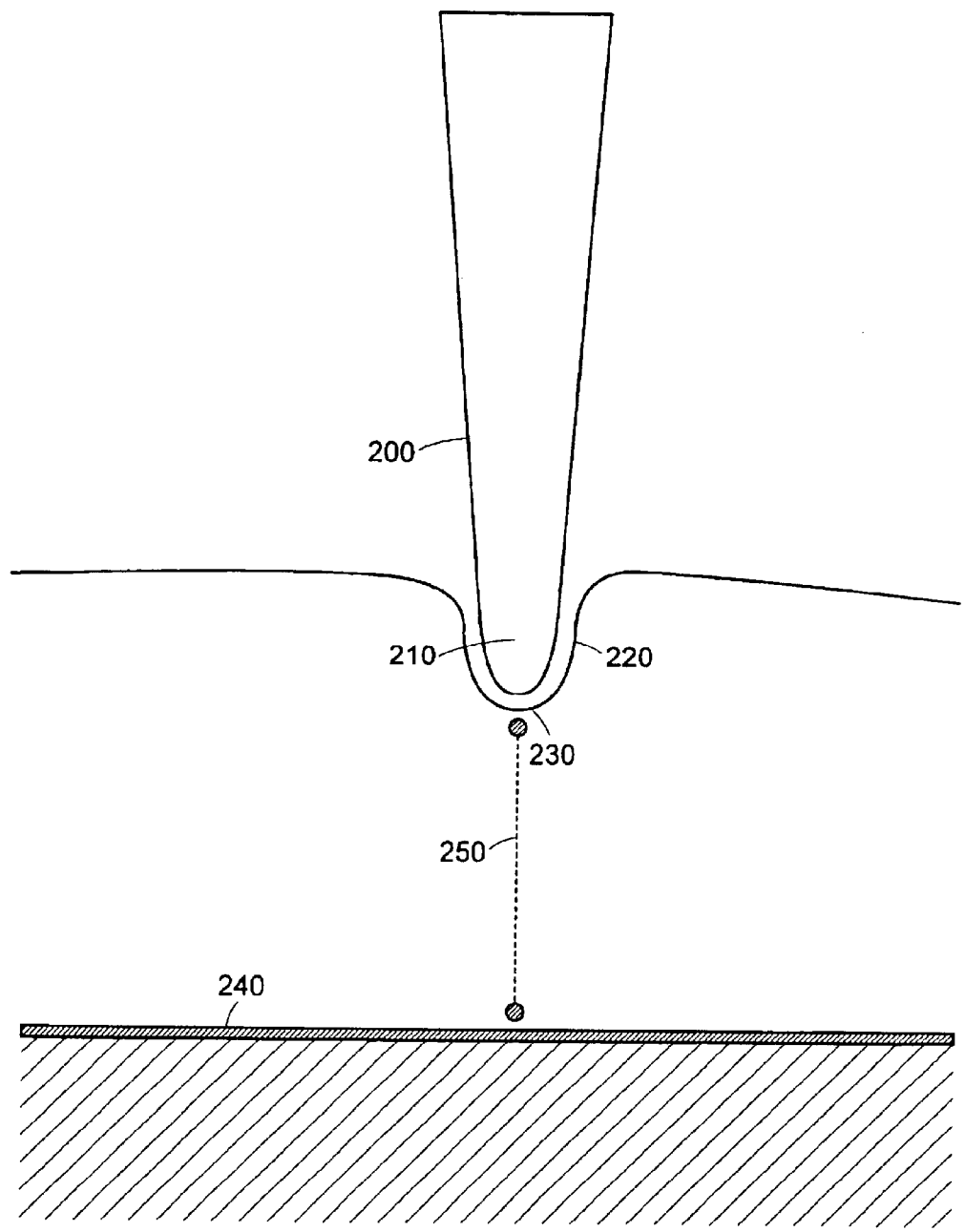
FIG. 2A shows a side view of an example of a cone shaped umbilicus positioning unit 200 comprising a tip 210 that fits in a human umbilicus 220 while permitting the ultrasonic probe to be in acoustic contact with the human abdomen. The ultrasonic probe transmits through the tip 210 and interrogates the distance between the skin/subcutaneous fat interface 230 and the subcutaneous fat/fascia or subcutaneous fat/muscle interface 240, thus yielding the thickness of the adipose tissue layer 250.

In one embodiment of the invention, an anatomically compatible ultrasonic probe is used for interrogation of the tissue subjacent to the umbilicus, e.g. adipose tissue or lean tissue. The anatomically compatible ultrasonic probe is shaped so that its external form follows the contour of the umbilicus in order to achieve a good fit between the probe and the umbilicus. For example, the anatomically compatible ultrasonic probe can be cone-shaped with a rounded tip at the transducer surface (FIG. 2A) or cylindrical with a rounded tip at the transducer surface. FIG. 2A shows an example of a cone shaped umbilicus positioning unit 200 comprising a tip 210 that fits in a human umbilicus 220 while permitting the ultrasonic probe to be in acoustic contact with the human abdomen. The ultrasonic probe transmits through the tip 210 and interrogates the distance between the skin/subcutaneous fat interface 230 and the subcutaneous fat/fascia or subcutaneous fat/muscle interface 240, thus yielding the thickness of the adipose tissue layer 250. In this embodiment, preferably the ultrasonic transducer is adapted for A-scan.

Typically, the length of the tip of an ultrasonic probe that is anatomically compatible with the umbilicus will be about 1–8 cm. The width of the portion of the tip is typically 1–3 cm. The cross-section of the ultrasonic probe can be round or elliptical. The cross-section of the ultrasonic probe near its tip can be expandable in order to adjust the probe for inter-individual variations in diameter of the umbilicus. For example, this can be achieved with a tip expander, such as an electromagnetic motor that moves portions of the external wall of the ultrasonic probe inwards or outwards, or by air or water inflation or deflation of an expandable cuff disposed near the tip of the ultrasonic probe. In this fashion, it is possible to achieve a good fit between the tip of the ultrasonic probe and the umbilicus in a wide range of different subjects. Alternatively, the tip of the ultrasonic probe can be exchangeable and the operator can select a probe tip with an external shape and a diameter and cross-section that provides a good anatomic fit and good acoustic coupling with the umbilicus of a given subject. In another embodiment, the operator can also dispose spacers around the circumference of the ultrasonic probe in order to achieve a good fit between the tip of the ultrasonic probe and the umbilicus.

Typically, a small amount of acoustic coupling gel is applied to the tip of the ultrasonic probe. If self-measurements are performed, saliva can be used in order to achieve acoustic coupling between the tip of the ultrasonic probe and the subject's skin. Alternatively, the external surface of the tip of the ultrasonic probe can consist of any current or future material that has a low impedance mismatch relative to skin, preferably human skin, thereby obviating the need for an acoustic coupling gel or other acoustic coupling medium.

To use a dedicated umbilicus probe of the invention, the tip of the ultrasonic probe is inserted into the umbilicus. Once the tip of the ultrasonic probe reaches the backwall of the umbilicus, an ultrasonic measurement of the thickness of the subjacent tissue, e.g. adipose tissue or muscle tissue, is performed. The umbilicus positioning unit can include a pressure sensor to detect, directly or indirectly, pressure on a face of the positioning unit.

Figure 2B:
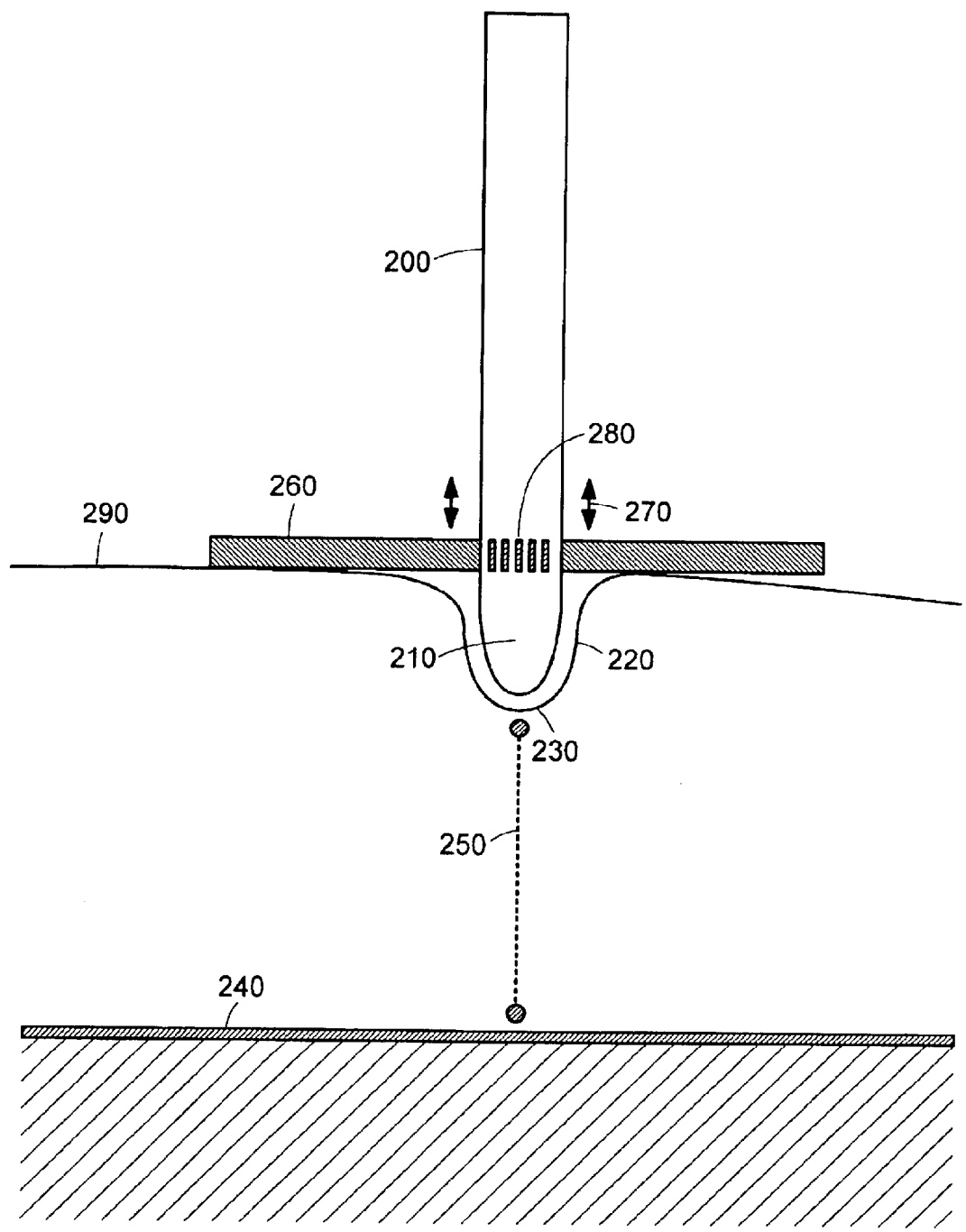
FIG. 2B shows a side view of a modification of the umbilicus positioning unit presented in FIG. 2A. The housing of the umbilicus positioning unit 200 is cylindrically shaped and comprises a tip 210 that fits in a human umbilicus 220 while permitting the ultrasonic probe to be in acoustic contact with the human abdomen. The ultrasonic probe transmits through the tip 210 and interrogates the distance between the skin/subcutaneous fat interface 230 and the subcutaneous fat/fascia or subcutaneous fat/muscle interface 240, thus yielding the thickness of the adipose tissue layer 250. The umbilicus positioning unit is designed with a securing member 260 with a friction fit for the tip 210. The tip 210 and the enclosed ultrasonic probe can be engaged with, or glide through 270, an opening 280 in the securing member 260. The securing member 260 stabilizes the umbilicus positioning unit against the abdominal wall 290.

In another embodiment of the invention, the ultrasonic probe may be attached to a securing member that helps stabilize the ultrasonic probe against the abdominal wall (FIG. 2B). FIG. 2B shows a side view of a modification of the umbilicus positioning unit presented in FIG. 2A. The housing of the umbilicus positioning unit 200 is cylindrically shaped and comprises a tip 210 that fits in a human umbilicus 220 while permitting the ultrasonic probe to be in acoustic contact with the human abdomen. The ultrasonic probe transmits through the tip 210 and interrogates the distance between the skin/subcutaneous fat interface 230 and the subcutaneous fat/fascia or subcutaneous fat/muscle interface 240, thus yielding the thickness of the adipose tissue layer 250. The umbilicus positioning unit is designed with a securing member 260 with a friction fit for the tip 210. The tip 210 and the enclosed ultrasonic probe can be engaged with, or glide through 270, an opening 280 in the securing member 260. The securing member 260 stabilizes the umbilicus positioning unit against the abdominal wall 290.

The securing member can consist of a flat plate that accommodates the ultrasonic probe centrally (FIG. 2B). Alternatively, the securing member can have a slightly curved shaped that follows the contour of the abdominal wall. The shape of the securing member may be adjustable, for example with use of a deformable plastic material. Alternatively, securing members can be made available with different sizes and shapes in order to achieve a good fit between the securing member and the abdominal wall surrounding the umbilicus. The distance between the surface of the securing member that is in contact with the subject's skin and the tip of the ultrasonic probe can be adjusted for the subject's body habitus and the depth of the umbilicus. For example, the ultrasonic probe can have a friction fit with the securing member. In subjects with a shallow umbilicus, a short distance will be selected between the surface of the securing member and the tip of the ultrasonic probe. In subjects with a deep umbilicus, the distance between the surface of the securing member and the tip of the ultrasonic probe will be increased in order to (a) achieve a good anatomic fit between the tip of the ultrasonic probe and the skin in the umbilicus and (b) to decrease the possibility of air inclusion between the transducer surface and the skin which can otherwise lead to erroneous measurements. The use of a securing member stabilizing the ultrasonic probe against the abdominal wall helps to position the ultrasonic probe at an angle of 90 degrees or near 90 degrees relative to the abdominal wall. In this fashion, it is possible to achieve ultrasonic probe angles and, thus, ultrasonic interrogation angles that are perpendicular or near perpendicular to the abdominal wall and the interrogated tissue layer. Thus, artifacts arising from non-perpendicular ultrasonic probe alignment such as artificial overestimation of tissue layer thickness, e.g. adipose tissue, and, for example, resultant overestimation of body fat can be avoided or reduced.

In many embodiments, it is preferable to use an ultrasonic transmission angle of 90 degrees. If the transmission angle is 90 degrees or near 90 degrees, the ultrasonic beam approaches an orthogonal position relative to the tissue plane. Preferably, ultrasonic measurements are performed when the ultrasonic beam is orthogonal to the plane of the tissue.

However, in another embodiment of the invention, the transmission angle is significantly different from about 90 degrees, for example it is about 80 degrees, more preferably about 70 degrees, even more preferably about 60 degrees. By using transmission angles other than 90 degrees, it is possible to interrogate a tissue plane that extends superior, inferior, medial or lateral of the umbilicus. In measuring body fat, this type of interrogation can be preferable in subjects who have an inhomogeneous distribution of subcutaneous fat. This type of interrogation is especially relevant for studies of the same subject over time, since the relative layer thickness at different angles may assess adipose deposition at different locations with a minimum of positioning artifacts. For example, a 60 degree transmission angle in superoinferior direction (from the skin to the adipose tissue layer) can be selected in a subject who has a greater thickness of the adipose tissue layer inferior to the umbilicus.

Furthermore, the invention provides for measurement of object layer thickness, e.g. adipose and lean tissue thickness, using transmission angles different from 90 degrees and oriented along different anatomic directions. For example, measurements of object layer thickness can be performed with a transmission angle of 60 degrees with the beam initially pointing in inferosuperior direction (from the skin to the subjacent tissue layer) for measurement of a tissue plane that extends superior of the umbilicus. The measurement can then be repeated again with the same transmission angle, in this example of 60 degrees, but with the beam now pointing in superoinferior direction (from the skin to the subjacent tissue layer) for measurement of a tissue plane that extends inferior of the umbilicus.

Optionally, the measurement can then be repeated again with the same transmission angle, in this example of 60 degrees, but with the beam now pointing in mediolateral direction towards the subject's right side (from the skin to the subjacent tissue layer) for measurement of a tissue plane that extends to the right side of the umbilicus. The measurement can then be repeated with the same transmission angle, in this example of 60 degrees, but with the beam now pointing in mediolateral direction towards the subject's left side (from the skin to the subjacent tissue layer) for measurement of a tissue plane that extends to the left side of the umbilicus. The different measurements of object layer thickness, e.g. adipose tissue or lean tissue thickness, can be compared in order to detect inhomogeneities in object layer thickness, e.g. variations in adipose tissue thickness and subcutaneous fat distribution.

Additionally, since the beam angulation is known, measured reflective distances can be corrected for parallax error resulting from beam angulation and reflective distance with a 90 degree transmission angle can be estimated (see also PCT patent application PCT/US97/18993).

Such comparisons can also be useful to detect any shifts in adipose tissue layer thickness during a diet or a nutritional regimen. For example, prior to initiation of a diet or a nutritional regimen, a subject may have a greater adipose tissue thickness inferior to the umbilicus than superior to the umbilicus. During or after a diet or nutritional regimen, the same subject can demonstrate a more homogeneous distribution of para-umbilical subcutaneous fat, e.g. similar subcutaneous adipose tissue thickness inferior and superior to the umbilicus.

In another embodiment of the invention, the measurement results can be averaged. Averaging of multiple measurement results can be particularly advantageous when the subject is monitored longitudinally over time in order to achieve greater consistency of the measurements. Longitudinal monitoring of adipose tissue layer thickness is, for example, desirable during a diet or a nutritional regimen. Longitudinal monitoring of muscle tissue thickness is, for example, desirable during a physical exercise program or in patients with metabolic or other disturbances with suspected tissue wasting.

Measurements obtained at the different sites or the average of the measurements can be stored in analog or digital format for comparison to prior measurements or follow-up measurements before or after the subject undergoes a diet, a nutritional regimen, or an exercise program.

The invention provides for a computational unit that is capable of processing ultrasonic signals. The present invention includes computer programs for (a) calculating layer thickness in a subject based on ultrasonic signals, particularly adipose or lean tissue layer thickness, (b) monitoring longitudinal changes in object layer thickness, e.g. adipose and lean tissue layer thickness, (c) averaging results obtained at different anatomic sites and different transmission angles and (d) providing estimates of body composition, such as total body fat or percent body fat based on ultrasonic measurements of adipose tissue layer thickness. The computer program can be stored on any storage device such as a chip, hard drive or floppy disc. The program can be used in conjunction with a computational unit and integrated into such a unit or it can be a separate unit compatible with computers, such as personal computers.

The present invention provides also a hand-held ultrasonic system that includes an ultrasonic probe for transmitting and receiving ultrasonic waves for adipose or lean tissue measurement, an electronic operating unit to control and process ultrasonic wave generation and detection, and a display to communicate adipose or lean tissue measurements to the operator. The hand held ultrasonic system can be battery powered. The handheld, ultrasonic system can have an ergonomic grip.

4.0 Anatomically Compatible Ulteasonic Probe Holder Devices

Ultrasonic measurements of object layer thickness have been used in the past in multiple different anatomic locations interrogating different tissue layers, e.g. adipose tissue and lean tissue. However, although variations in ultrasonic probe position can reduce the reproducibility of ultrasonic measurements of object layer thickness, the use of anatomically compatible ultrasonic probe holders for improving the reproducibility of measurements of object layer thickness has not been described previously.

The present invention provides for methods and devices that improve the reproducibility of ultrasonic measurements of object layer thickness, such as adipose or lean tissue in a human. In one embodiment of the invention, an anatomically compatible ultrasonic probe holder is used for positioning of an ultrasonic probe for measurement of object layer thickness, e.g. thickness of adipose tissue or muscle tissue in a human. Such holders typically comprise an anatomic reference member. The anatomically compatible ultrasonic probe holder is shaped so that its external form follows the contour of the body surface in the interrogated region. For example, in the region of the thigh or the anterior superior iliac spine and iliac crest, the anatomically compatible ultrasonic probe holder can have a concave or a semicircular shape. The degree of concavity or the radius of the semicircle can be varied to adjust for inter-individual variations in contour of the body surface. Variation of the concavity or or convexity can be, for example, achieved with use of one or more hinges deployed along the length of the ultrasonic probe holder or with use of a deformable plastic material or metal.

Alternatively, a set of differently shaped ultrasonic probe holders each with fixed size and shape can be used and the patient or the physician can select the one that provides a good fit, good stabilization of the probe against the skin in order to decrease errors in probe angulation, and good anatomic coupling for a given anatomic region in each individual patient. The ultrasonic probe holder can also be pliable or deformable so that the patient or the physician can produce a form that matches the contour of the body surface in the interrogated region using deformable plastic materials or metal.

In the thigh region, the surface of the ultrasonic probe holder can be 5 cm, more preferably 10 cm long in the mediolateral direction and 1–3 cm, more preferably 3–6 cm wide in superoinferior direction. A width of 3–6 cm in the superoinferior direction is preferable since it helps stabilize the ultrasonic probe holder against the thigh thereby decreasing potential errors in angulation of the ultrasonic probe. In the region of the anterior superior iliac spine and the iliac crest, the surface of the ultrasonic probe holder can be 5 cm, more preferably 10 cm long in the mediolateral direction and 2–4 cm, more preferably 4–8 cm wide in superoinferior direction. A width of 4–8 cm in the superoinferior direction is preferable since it helps stabilize the ultrasonic probe holder against the abdominal wall in the region of the anterior superior iliac spine and the iliac crest thereby decreasing potential errors in angulation of the ultrasonic probe.

In another embodiment, the ultrasonic probe holder can have an anatomical reference member with a variable length, for example with use of an extendable member. Such extendable members can be composed of multiple interlocking or telescoping segments. Each segment may fit inside of the other.

Use of an anatomically compatible ultrasonic probe holder can help to achieve more reproducible positioning of the ultrasonic probe over the same anatomic region when repeated measurements are performed. Use of an anatomically compatible ultrasonic probe holder can also help to avoid positioning of the probe at angles other than 90 degrees relative to the body surface or the interrogated tissue. Ultrasonic probe positioning at angles other than 90 degrees relative to the body surface or the interrogated tissue can lead to overestimation of object layer thickness (see also PCT patent application PCT/US97/18993).

In another embodiment of the invention, an anatomically compatible ultrasonic probe holder with a shape that follows the contour of an external landmark is used. The external landmark can be identified by the operator visually as a protuberance or indentation in the outer contour of the subject's body or it can be identified by the operator using manual palpation and compression of the skin, subcutaneous tissues, and muscle. The external reference landmark can be composed of soft-tissue, e.g. skin and subcutaneous fat in the umbilicus, or of dense tissue, e.g. cartilage or bone. External reference landmarks include but are not limited to the umbilicus, the acromioclavicular joint, the scapular spine, the xiphoid process, the superior aspect of the iliac crest, the anterior superior iliac spine, the anterior inferior iliac spine, the posterior superior iliac spine, or the greater trochanter.

Other external landmarks can include, but are not limited to, the knee joint space, the patella, the anterior tibia, the medial and lateral malleolus, the metatarsophalangeal joints, the interphalangeal joints of the foot, the olecranon, the distal radius, the distal ulna, the carpometacarpal joints, the metacarphophalangeal joints, and the interphalangeal joints of the hand.

Use of an external landmark as a reference for positioning of an ultrasonic probe holder helps to improve the reproducibility of ultrasonic probe positioning and helps interrogating the same tissue area and volume when repeated ultrasonic measurements are performed. Use of an anatomically compatible ultrasonic probe holder that follows the contour of the anatomic landmark can improve the reproducibility of ultrasonic measurements of object layer thickness, e.g. adipose tissue thickness or lean tissue thickness. Preferably, in most embodiments the ultrasonic transducer is oriented to interrogate a tissue at a predetermined distance from a site used to locate an anatomical reference member.

Figure 3A:
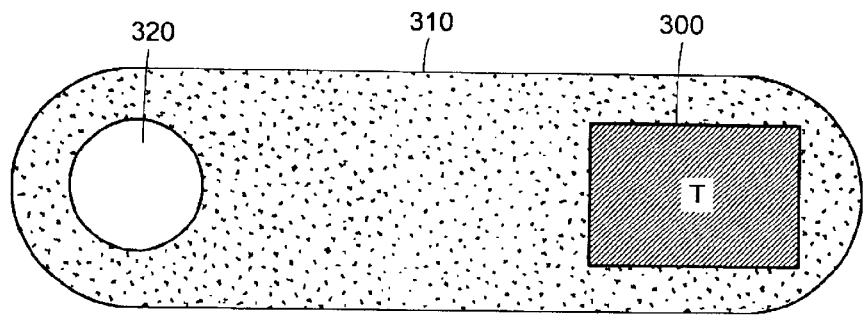
FIG. 3A shows a view from the top of an example of a handheld transducer (T) 300 disposed in an anatomical reference member 310. The anatomical reference member 310 comprises a ring 320 disposed with respect to the ultrasonic transducer 300 at a predetermined distance. The ring 320 permits the operator to controllably position the anatomical reference member 310 and the ultrasonic transducer 300 with respect to the desired anatomical region.

FIG. 3A shows an example of a handheld transducer (T) 300 disposed in an anatomical reference member 310. The anatomical reference member 310 comprises a ring 320 disposed with respect to the ultrasonic transducer 300 at a predetermined distance. The ring 320 permits the operator to controllably position the anatomical reference member 310 and the ultrasonic transducer 300 with respect to the desired anatomical region. For example, the operator can palpate the anterior superior iliac spine in a subject. The ultrasonic probe holder is then placed so that the ring opening 320 is positioned over the anterior superior iliac spine and the ultrasonic transducer 300 is, for example, located superiorly towards the subject's head. The operator will then confirm correct placement of the ultrasonic probe holder by palpating the anterior superior iliac spine again through the ring opening 320. Once correct placement of the ultrasonic probe holder has been confirmed, the measurement will be obtained. Measurements can be repeated with the transducer pointing medially, laterally, or inferiorly.

Figure 3B:
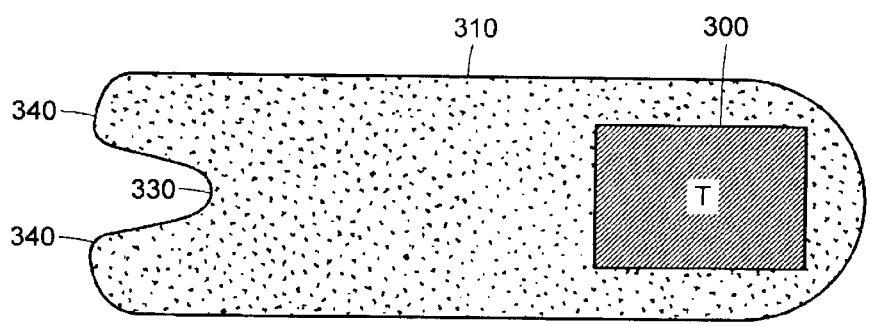
FIG. 3B shows a view from the top of a modification of the embodiment presented in FIG. 3A. The anatomical reference member 310 comprises a groove 330 disposed with respect to the ultrasonic transducer 300 at a predetermined distance. The groove 330 permits the operator to controllably position the anatomical reference member 310 and the ultrasonic transducer 300 with respect to the desired anatomical region. The edges 340 of the anatomical reference member 310 adjacent to the groove 330 can be used to locate the anatomical reference member and the ultrasonic transducer against an external landmark, such as an umbilicus.

FIG. 3B shows a modification of the embodiment presented in FIG. 3A. The anatomical reference member 310 comprises a groove 330 disposed with respect to the ultrasonic transducer 300 at a predetermined distance. The groove 330 permits the operator to controllably position the anatomical reference member 310 and the ultrasonic transducer 300 with respect to the desired anatomical region. The edges 340 of the anatomical reference member 310 adjacent to the groove 330 can be used to locate the anatomical reference member and the ultrasonic transducer against an external landmark. This configuration of an ultrasonic probe holder can, for example, also be applied to the region of the anterior superior iliac spine. In this case, the operator will palpate the anterior superior iliac spine. The ultrasonic probe holder is then placed so that the groove 330 is positioned over the anterior superior iliac spine and the ultrasonic transducer 300 is, for example, located superiorly towards the subject's head. The operator will then confirm correct placement of the ultrasonic probe holder by palpating the anterior superior iliac spine again and reconfirming placement of the groove of the ultrasonic probe holder over this landmark. Once correct placement of the ultrasonic probe holder has been confirmed, the measurement can be obtained.

This configuration of an ultrasonic probe holder is also applicable to measurements in the region surrounding the xiphoid process. In this case, the operator will palpate the xiphoid process. The ultrasonic probe holder is then placed so that the groove 330 is positioned over the xiphoid process and ultrasonic transducer 300 is, for example, located inferiorly towards the subject's feet. The operator will then confirm correct placement of the ultrasonic probe holder by palpating the xiphoid process again and reconfirming placement of the groove of the ultrasonic probe holder over this landmark. Once correct placement of the ultrasonic probe holder has been confirmed, the measurement can be obtained.

In one embodiment of the invention, an anatomically compatible ultrasonic probe holder is used for interrogation of the paraumbilical tissue, e.g. adipose tissue or lean tissue. The anatomically compatible ultrasonic probe holder is shaped so that its external form follows the contour of the umbilicus in order to achieve a good fit between the probe holder and the umbilicus. Such holders typically include an umbilicus positioning unit. For example, the ultrasonic probe holder can be cone shaped with a rounded tip (FIG. 4A) or cylindral with a rounded tip.

Figure 4A:
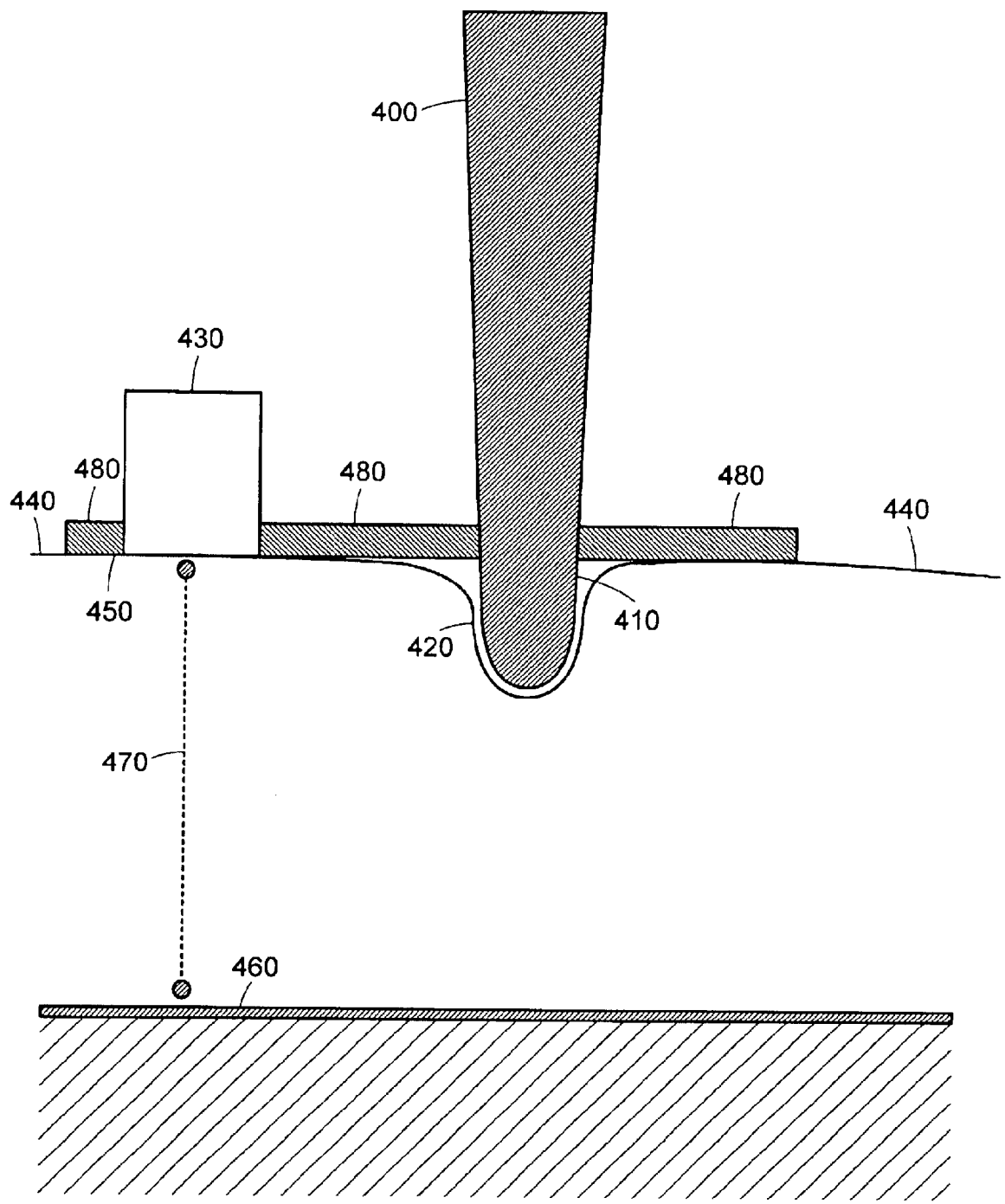
FIG. 4A shows side view of an example of a handheld probe with an umbilicus positioning unit. The housing of the umbilicus positioning unit 400 is cone shaped and comprises a tip 410 that fits in a human umbilicus 420. The ultrasonic probe 430 is in acoustic contact with the skin 440 of the abdomen and is located at a predetermined distance from the tip 410 of the umbilicus positioning unit 400. The ultrasonic probe transmits at a site substantially different from the tip 410 and interrogates the distance between the skin/subcutaneous fat interface 450 and the subcutaneous fat/fascia or subcutaneous fat/muscle interface 460, thus yielding the thickness of the adipose tissue layer 470. The umbilicus positioning unit is designed with a securing member 480 which stabilizes the umbilicus positioning unit against the skin of the abdominal wall 440.

FIG. 4A shows side view of an example of a handheld probe with an umbilicus positioning unit. The housing of the umbilicus positioning unit 400 is cone shaped and comprises a tip 410 that fits in a human umbilicus 420. The ultrasonic probe 430 is in acoustic contact with the skin 440 of the abdomen and is located at a predetermined distance from the tip 410 of the umbilicus positioning unit 400. The ultrasonic probe transmits at a site substantially different from the tip 410 and interrogates the distance between the skin/subcutaneous fat interface 450 and the subcutaneous fat/fascia or subcutaneous fat/muscle interface 460, thus yielding the thickness of the adipose tissue layer 470. The umbilicus positioning unit is designed with a securing member 480 which stabilizes the umbilicus positioning unit against the skin of the abdominal wall 440.

Typically, the length of the tip of an ultrasonic probe holder of an ultrasonic probe holder that is anatomically compatible with the umbilicus will be about 1–8 cm. The width of the portion of the tip is typically 1–3 cm. The cross-section of the ultrasonic probe holder can be round or elliptical. The cross-section of the ultrasonic probe holder near its tip can be expandable in order to adjust the probe for interindividual variations in diameter of the umbilicus. For example, this can be achieved with mechanical means, with use of an electromagnetic motor that moves portions of the external wall of the ultrasonic probe holder inwards or outwards, or by air or water inflation or deflation of an expandable cuff disposed near the tip of the ultrasonic probe holder. In this fashion, it is possible to achieve a good fit between the tip of the ultrasonic probe holder and the umbilicus in a wide range of different subjects. Alternatively, the tip of the ultrasonic probe holder can be exchangeable and the operator can select a tip with an external shape and a diameter and cross-section that provides the best anatomic fit for the umbilicus of a given subject. In another embodiment, the operator can also dispose spacers around the circumference of the ultrasonic probe holder in order to achieve a good fit between the tip of the ultrasonic probe holder and the umbilicus.

The tip of the ultrasonic probe holder can be inserted into the umbilicus. The ultrasonic probe can be located either superior (FIG. 4A), inferior, medial or lateral to the umbilicus. Once the ultrasonic probe holder is positioned inside the umbilicus, an ultrasonic measurement of object layer thickness, e.g. adipose tissue or muscle tissue, is performed. The ultrasonic probe holder can include a pressure sensor to detect, directly or indirectly, pressure on a face of the positioning unit.

Typically, the ultrasonic probe holder has a flat undersurface that helps stabilize the ultrasonic probe holder and the attached ultrasonic probe against the abdominal wall (FIG. 4A). Alternatively, the ultrasonic probe holder can have a slightly curved shaped that follows the contour of the abdominal wall. The shape of the ultrasonic probe holder may be adjustable, for example with use of a deformable plastic material. The distance between the surface of the ultrasonic probe holder that is in contact with the subject's skin and the tip of the ultrasonic probe holder can be adjusted for the subject's body habitus and the depth of the umbilicus. Alternatively, the ultrasonic probe can be made detachable from the ultrasonic probe holder and the ultrasonic probe holder can be made available with different sizes and shapes in order to achieve a good fit between ultrasonic probe holder and the abdominal wall and the umbilicus. For example, in subjects with a shallow umbilicus, the tip of the ultrasonic probe holder that protrudes into the umbilicus is preferably short. In subjects with a deep umbilicus, the tip of the ultrasonic probe holder that protrudes into the umbilicus is preferably long. Stabilization of the ultrasonic probe holder against the abdominal wall helps to position the ultrasonic probe at an angle of 90 degrees or near 90 degrees relative to the abdominal wall. In this fashion, it is possible to achieve ultrasonic probe angles and, thus, ultrasonic interrogation angles that are perpendicular or near perpendicular to the abdominal wall and the interrogated tissue layer. Thus, artifacts arising from non-perpendicular ultrasonic probe alignment, such as artificial overestimation of tissue layer thickness, e.g. adipose tissue, and, for example, resultant overestimation of body fat can be avoided or reduced.

In another embodiment of the invention, multiple measurements of object layer thickness, e.g. adipose or lean tissue layer thickness, are performed at different ultrasonic probe positions. For example, the tip of the ultrasonic probe holder is advanced into the umbilicus, the probe is positioned superior to the umbilicus, and an ultrasonic measurement of object layer thickness, e.g. adipose tissue layer thickness or muscle layer thickness, is performed with the ultrasonic probe in this position. The ultrasonic probe holder and the attached ultrasonic probe are then rotated 90 degrees to the subject's right side and the measurement is repeated, now with the ultrasonic probe positioned at the same superoinferior level than the umbilicus but positioned on the subject's right side lateral to the umbilicus. The ultrasonic probe holder and the attached ultrasonic probe are then rotated 90 degrees inferiorly and the measurement is repeated, now with the ultrasonic probe positioned inferior to the umbilicus. The ultrasonic probe holder and the attached ultrasonic probe are then rotated 90 degrees to the subject's left side and the measurement is repeated, now with the ultrasonic probe positioned at the same superoinferior level than the umbilicus but positioned on the subject's left side lateral to the umbilicus. In this setting, the ultrasonic transducer can be placed at least about 1 cm distant from the umbilicus, more preferably about 2 cm distant from the umbilicus, even more preferably about 5 cm from the umbilicus, although measurements at greater and lesser distance can also be performed.

The measurements of object layer thickness, e.g. adipose tissue or lean tissue thickness, obtained at the different locations can be compared in order to detect inhomogeneities in object layer thickness, e.g. variations in adipose tissue thickness and subcutaneous fat distribution. Such comparisons can also be useful to detect any shifts in adipose tissue layer thickness during a diet or a nutritional regimen. For example, prior to initiation of a diet or a nutritional regimen, a subject may have a greater adipose tissue thickness inferior to the umbilicus than superior to the umbilicus. During or after a diet or nutritional regimen, the same subject can demonstrate a more homogeneous distribution of para-umbilical subcutaneous fat, e.g. similar subcutaneous adipose tissue thickness inferior and superior to the umbilicus.

In another embodiment of the invention, the measurement results obtained in the different locations can be averaged. Averaging of multiple measurement results can be particularly advantageous when the subject is monitored longitudinally over time in order to achieve greater consistency of the measurements. Longitudinal monitoring of adipose tissue layer thickness is, for example, desirable during a diet or a nutritional regimen. Longitudinal monitoring of muscle tissue thickness is, for example, desirable during a physical exercise program or in patients with metabolic or other disturbances with suspected tissue wasting.

Figure 4B:
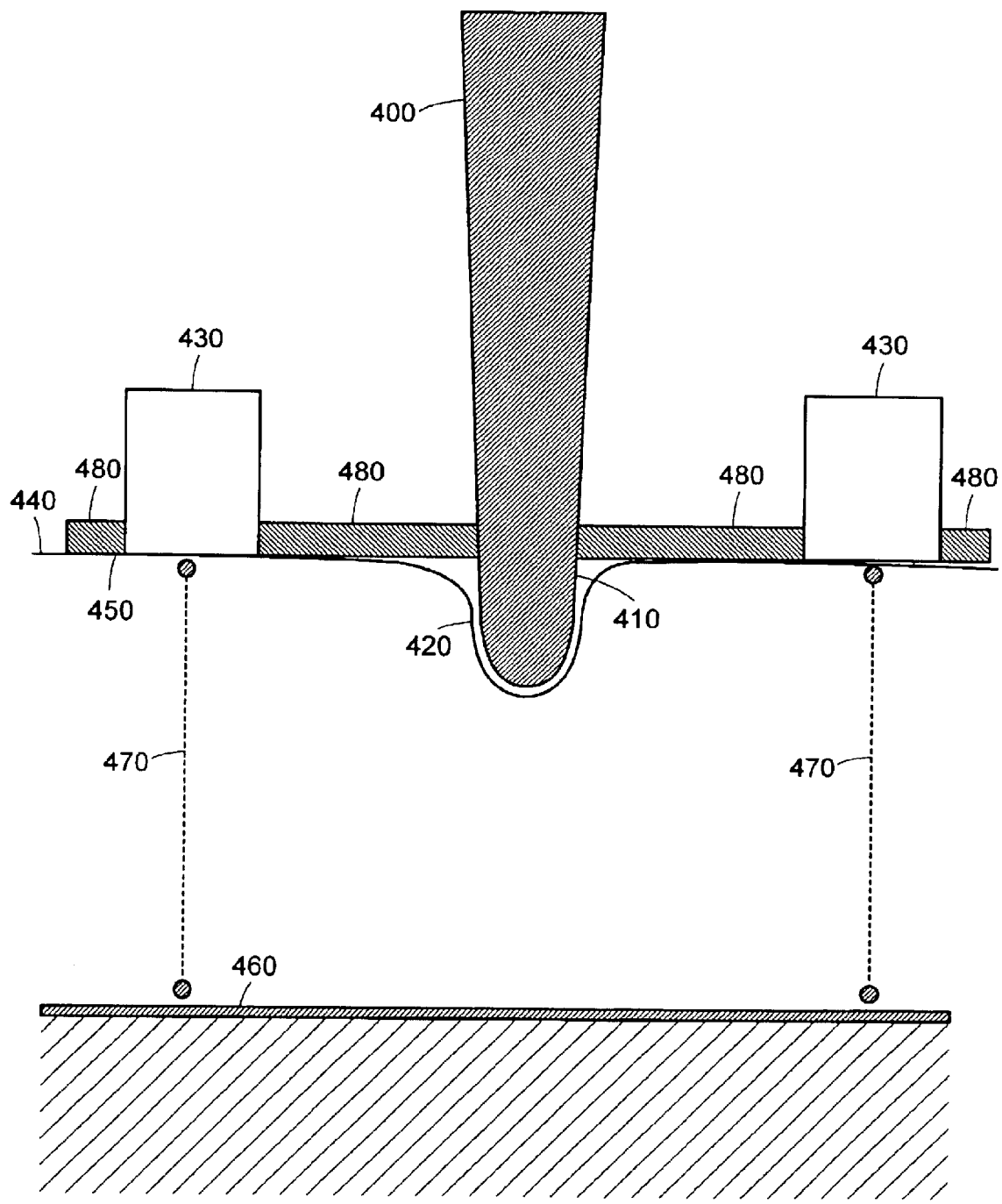
FIG. 4B shows a side view of a modification of the embodiment presented in FIG. 4A with two ultrasonic probes rather than one ultrasonic probe 430 disposed at predetermined distances from the tip 410 of the umbilicus positioning unit 400. Both ultrasonic probes 430 interrogate the adipose tissue layer thickness 470 at a site substantially different from the umbilicus 420 and the tip 410 of the umbilicus positioning unit 400. In this fashion, adipose tissue layer thickness 470 can be simultaneously interrogated superior and inferior to the umbilicus or lateral to the left of the umbilicus and lateral to the right of the umbilicus.

In another embodiment of the invention, more than one ultrasonic probe can be attached to the ultrasonic probe holder. The different ultrasonic probes can be deployed superior and inferior to the umbilicus or lateral to the right, and lateral to the left of the umbilicus (FIGS. 4B and C). Additionally, the tip of one additional ultrasonic probe can be positioned inside the umbilicus.

FIG. 4B shows a side view of a modification of the embodiment presented in FIG. 4A with two ultrasonic probes rather than one ultrasonic probe 430 disposed at predetermined distances from the tip 410 of the umbilicus positioning unit 400. Both ultrasonic probes 430 interrogate the adipose tissue layer thickness 470 at a site substantially different from the umbilicus 420 and the tip 410 of the umbilicus positioning unit 400. In this fashion, adipose tissue layer thickness 470 can be simultaneously interrogated superior and inferior to the umbilicus or lateral to the left of the umbilicus and lateral to the right of the umbilicus.

Figure 4C:
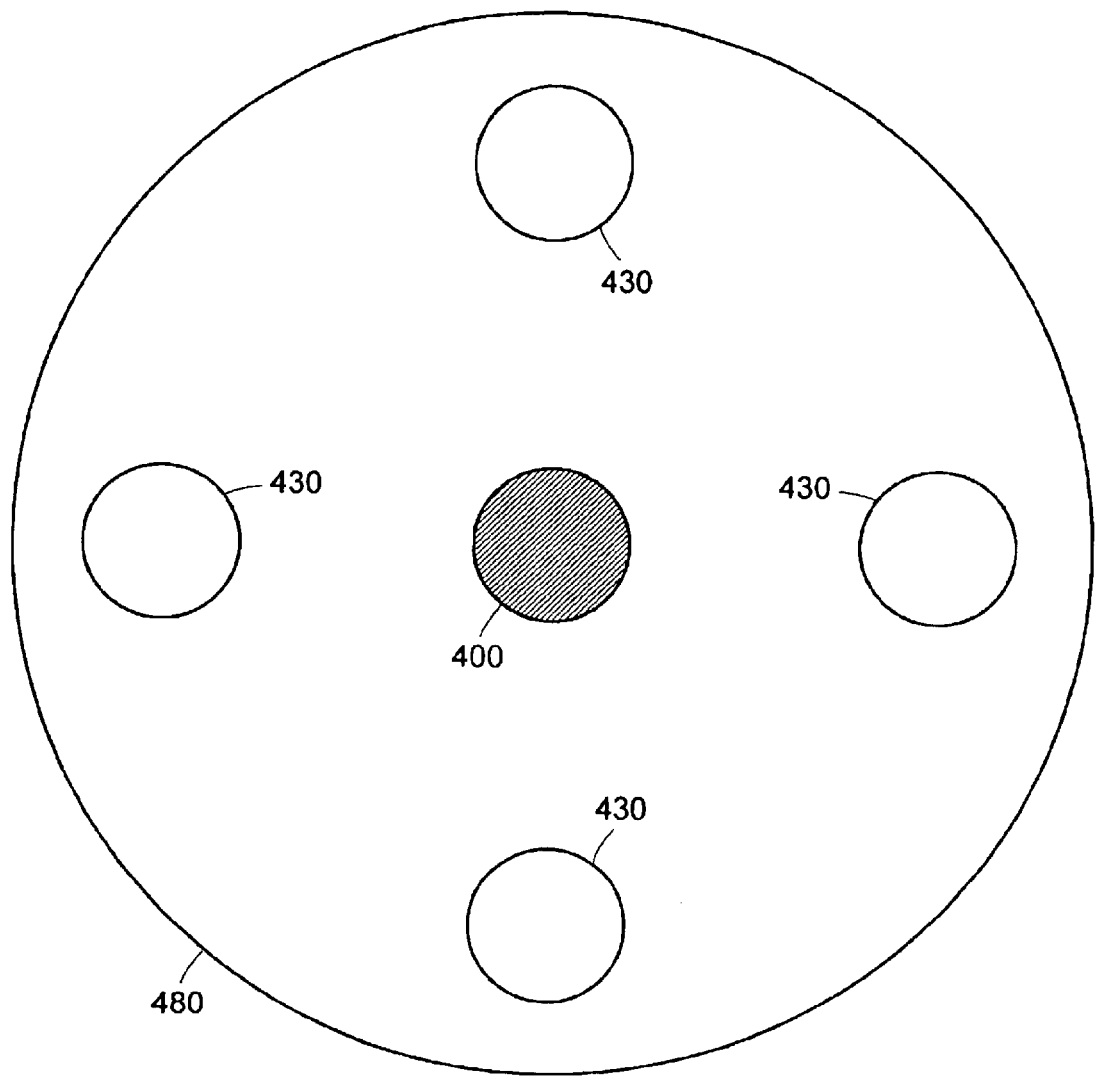
FIG. 4C shows a view from the top of a modification of the embodiments presented in FIGS. 4A and 4B. The umbilicus positioning unit 400 is located in the center of a securing member 480 which stabilizes the umbilicus positioning unit 400 and the ultrasonic probes 430 against the abdominal wall (not shown). Four ultrasonic probes 430 are disposed at predetermined distances from the tip (not shown) of the umbilicus positioning unit 400. In this fashion, adipose tissue layer thickness can be simultaneously interrogated superior, inferior, lateral to the left, and lateral to the right of the umbilicus.

FIG. 4C shows a view from the top of a modification of the embodiments presented in FIGS. 4A and 4B. The umbilicus positioning unit 400 is located in the center of a securing member 480 which stabilizes the umbilicus positioning unit 400 and the ultrasonic probes 430 against the abdominal wall (not shown). Four ultrasonic probes 430 are disposed at predetermined distances from the tip (not shown) of the umbilicus positioning unit 400. In this fashion, adipose tissue layer thickness can be simultaneously interrogated superior, inferior, lateral to the left, and lateral to the right of the umbilicus.

Any other spatial arrangement of the ultrasonic probes is possible, if desired. Optionally, multiple ultrasonic probes can be deployed around the umbilicus in a ring-like or annular fashion (FIG. 4D).

Figure 4D:
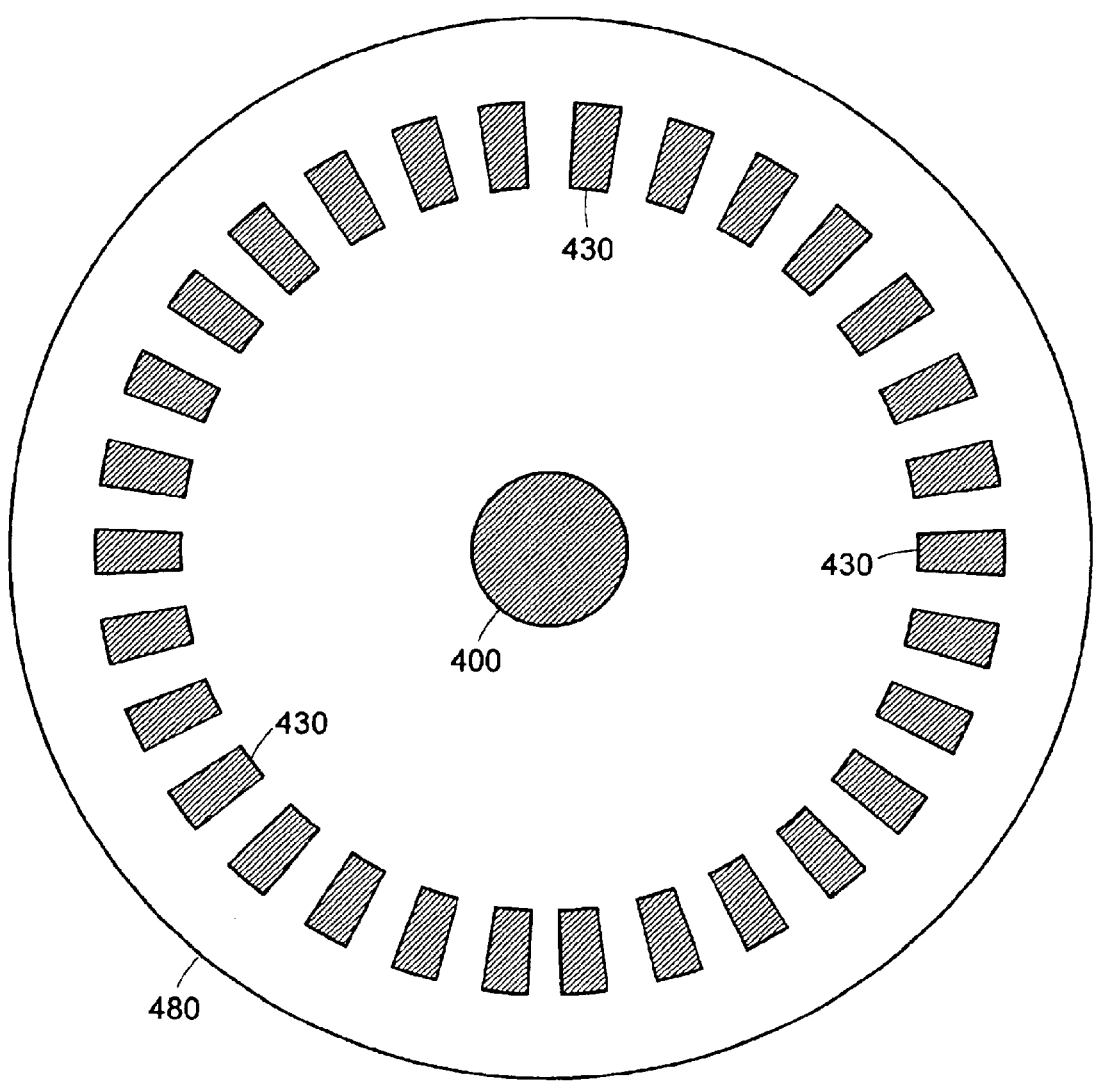
FIG. 4D shows a view from the top of a modification of the embodiment shown in FIG. 4C. An annular array of ultrasonic probes 430 is disposed at predetermined distances from the tip (not shown) of the umbilicus positioning unit 400.

FIG. 4D shows a view from the top of a modification of the embodiment shown in FIG. 4C. An annular array of ultrasonic probes 430 is disposed at predetermined distances from the tip (not shown) of the umbilicus positioning unit 400.

The ultrasonic probe units of the invention can contain one, two, three, four or more ultrasonic transducers.

Measurements of object layer thickness, e.g. adipose tissue or lean tissue layer thickness, obtained at the different ultrasonic probe positions can be compared to use as a method of detecting inhomogeneities in object layer thickness, e.g. variations in adipose tissue thickness and subcutaneous fat distribution. Alternatively, measurements of object layer thickness, e.g. adipose tissue or lean tissue layer thickness, obtained at the different ultrasonic probe positions can be averaged. Measurements obtained at the different sites or the average of the measurements can be stored in analog or digital format for comparison to prior measurements or follow-up measurements before or after the subject undergoes a diet, a nutritional regimen, or an exercise program.

The present invention provides also a hand-held ultrasonic system that includes an ultrasonic probe for transmitting and receiving ultrasonic waves for adipose or lean tissue measurement, an electronic operating unit to control and process ultrasonic wave generation and detection, an ultrasonic probe holder, and a display to communicate adipose or lean tissue measurements to the operator. The hand held ultrasonic system can be battery powered. The handheld ultrasonic system can have an ergonomic grip, preferably attached to the ultrasonic probe holder.

5.0 Kits and Programs for Health Related Measurements

The present invention includes kits for monitoring object layer thickness especially of biological layers and tissues, such as fat and lean tissue including muscle and bone. For example, the kits can include an ultrasonic system for measuring object layer thickness, and at least one of the following 1) nutritional supplements, 2) a nutrition plan, 3) a workout plan, 4) cardiovascular therapeutics, 5) weight loss agents, 6) prescription or over the counter drugs (including anti-cancer agents and hormones, e.g. steroids), 7) fitness equipment and 8) a health club membership.

EXAMPLES

The following materials and methods are exemplary of the materials and methods that can be used to achieve the results described herein. These prophetic examples are for illustrative purposes only, and are not to be construed as limiting the appended claims. One skilled in the art will readily recognize substitute materials and methods.

General Materials and Methods

In vivo ultrasonic measurements in the umbilical and paraumbilical region are performed using a first prototype ultrasonic system operating in A-scan mode consisting of one ultrasonic probe attached to an umbilicus ultrasonic probe holder. The ultrasonic system is capable of measuring distances between different acoustic/tissue interfaces based on analysis of signal amplitude versus time. The system can identify the signals arising from the skin/subcutaneous fat interface, the signals arising from the subcutaneous fat/fascia or subcutaneous fat/muscle interface and the signal arising from the muscle/fascia interfaces. The system performs an automatic time gain compensation in order to match the magnitude of the signal amplitude registered at the skin/subcutaneous fat interface and the signal amplitude registered at the subcutaneous fat/fascia or the subcutaneous fat/muscle interface and the signal amplitude registered at the muscle/fascia interfaces. For most applications, the system operates at a center frequency of 2MHz. In obese subjects, in whom the system fails to detect the signal amplitude arising from the subcutaneous fat/fascia or subcutaneous fat/muscle interface or the muscle/fascia interfaces, the ultrasonic system will switch to a center frequency of 1 MHz and repeat the analysis. As the interrogation frequency of the micro-transducer decreases, generally, the ability to resolve reflective surfaces at deeper depths improves. If the ultrasonic system still cannot identify the signal amplitude arising from the subcutaneous fat/fascia or the subcutaneous fat/muscle interface or the muscle/fascia interfaces, it emits an acoustic alarm informing the operator that the measurement failed. In this case, the system will perform a self-test. Additionally, the acoustic alarm indicates to the operator to check the testing conditions, e.g. if the amount of gel applied to the measurement site is sufficient, if interposed hair may have accounted for the problem etc. All measurements are expressed in mm.

The external shape and configuration of the first prototype ultrasonic system is similar to the one shown in FIG. 4A with an ultrasonic probe attached to an ultrasonic probe holder. The ultrasonic probe holder has a rounded tip so that its external form follows the contour of the umbilicus in order to achieve a good fit between the probe holder and the umbilicus. The tip of the ultrasonic probe holder is exchangeable. The operator can select a tip with an external shape, a length, and a diameter, and cross-section that provide the best anatomic fit for the umbilicus of a given subject. The tip of the ultrasonic probe holder is available in lengths ranging from 1–8 cm and widths ranging from 1–3 cm. The tip of the ultrasonic probe holder is available with a round and an elliptical cross-section. The handheld ultrasonic system has an ergonomic grip to facilitate use by an operator other than the subject and also to facilitate self-measurements. An acoustic coupling gel is applied to the surface of the ultrasonic probe in order to reduce the impedance mismatch between the surface of the ultrasonic probe and the skin. The tip of the ultrasonic probe holder is inserted into the umbilicus. The umbilicus serves as an external landmark which aids in achieving good reproducibility of ultrasonic measurements when repeat examination is performed at multiple time intervals.

The ultrasonic probe can be located either superior (FIG. 4A), inferior, medial, lateral, or at any other location relative to the umbilicus. The distance between the ultrasonic probe and the tip of the ultrasonic probe holder positioned inside the umbilicus is 5 cm. Using an extendable member, the distance between the ultrasonic probe and the tip of the ultrasonic probe holder can be increased to 10 cm. The standard ultrasonic probe holder has a flat undersurface. The ultrasonic probe can be detached from the ultrasonic probe holder. Ultrasonic probe holders are available in different sizes and shapes including curved shapes of different radii in order to achieve a good fit between the ultrasonic probe holder and the abdominal wall and the umbilicus. The undersurface of the ultrasonic probe holder is stabilized against the abdominal wall (FIG. 4A). Stabilization of the ultrasonic probe holder against the abdominal wall helps to position the ultrasonic probe at an angle of 90 degrees or near 90 degrees relative to the abdominal wall. In this fashion, it is possible to achieve ultrasonic probe angles and, thus, ultrasonic interrogation angles that are perpendicular or near perpendicular to the abdominal wall and the interrogated tissue layer. Thus, artifacts arising from non-perpendicular ultrasonic probe alignment such as artificial overestimation of tissue layer thickness, e.g. adipose tissue, and, for example, resultant overestimation of body fat can be avoided or reduced. Once the ultrasonic probe holder is positioned inside the umbilicus, an ultrasonic measurement of object layer thickness, e.g. adipose tissue or muscle tissue, is performed.

The ultrasonic system is handheld and battery powered. The battery compartment is integrated inside the grip portion of the ultrasonic probe. The ultrasonic system is designed with a central processing unit responsible for pulsing the ultrasonic transducer(s) and crystal(s), registering signals returned from the transducer, preamplification of the electronic signal, time gain compensation, signal compression, signal rectification, demodulation, and envelope detection, signal rejection, signal processing, analysis and display of tissue layer thickness measurements. The central processing unit is integrated inside the handheld device. Computer programs calculate adipose or muscle layer thickness based on ultrasonic signals, store the results for a given measurement site, date, and patient in a memory unit, monitor longitudinal changes in adipose tissue layer thickness, and average results obtained at different anatomic sites, and provide estimates of body composition such as total body fat or percent body fat based on patient weight and height and ultrasonic measurements of adipose tissue layer thickness. Patient weight and height are manually entered by the operator. Using manual input, different patients can be entered using initials and date of birth for patient identification and patients can be followed longitudinally over time. The device is capable of storing the results of up to 1000 measurements obtained at different time points and different sites in different subjects. An LCD display communicates measurement results and longitudinal trends over time to the operator.

The ultrasonic system has an electronic port that can be used to download the data into a PC or Macintosh based computer systems as well as handheld computer systems, such as the PalmPilot II (manufactured by U.S. Robotics) via an electronic cable. Alternatively, an infra red or a radiofrequency port can be used for data transfer. Computer software is available for these computer systems that provides for storage of measurement results, statistical analysis of longitudinal changes in adipose or muscle tissue thickness, total body fat, or percent body fat, as well as other parameters that can be derived, and generation of graphic presentations and charts displaying these parameters separately or together over time.

Ultrasonic measurements of object layer thickness in the umbilical and paraumbilical region can also be performed using a second prototype ultrasonic system. Unlike the first prototype ultrasonic system which is configured with only a single ultrasonic probe attached to an ultrasonic probe holder, the second prototype ultrasonic system has four ultrasonic probes attached to an ultrasonic probe holder similar to the device shown in FIG. 4C. The ultrasonic probe holder has a rounded tip so that its external form follows the contour of the umbilicus in order to achieve a good fit between the probe holder and the umbilicus. The tip of the ultrasonic probe holder is exchangeable. The operator can select a tip with an external shape, a length, and a diameter, and cross-section that provide the best anatomic fit for the umbilicus of a given subject. The tip of the ultrasonic probe holder is available in lengths ranging from 1–8 cm and widths ranging from 1–3 cm. The tip of the ultrasonic probe holder is available with a round and an elliptical cross-section.

The four ultrasonic probes are disposed in an equidistant fashion along the perimeter of the ultrasonic probe holder (FIG. 4C). In this fashion, adipose tissue thickness can be measured simultaneously, for example, superior, inferior, and lateral to the left and right side of the umbilicus. The four ultrasonic probes can be detached from the ultrasonic probe holder. Ultrasonic probe holders are available in different sizes and shapes including curved shapes of different radii in order to achieve a good fit between the ultrasonic probe holder and the abdominal wall and the umbilicus. The undersurface of the ultrasonic probe holder is stabilized against the abdominal wall. The basic configuration and all signal processing and data analysis aspects of the ultrasonic probes used in the second prototype ultrasonic system are otherwise similar or identical to that used in the first prototype ultrasonic system described above.

Ultrasonic measurements of object layer thickness in the suprailiac and iliac crest region can be performed using a third prototype ultrasonic system. Similar to the first and the second prototype ultrasonic system which are anatomically compatible for measurement in the paraumbilical region, the third prototype ultrasonic system includes an ultrasonic probe holder designed to achieve anatomic compatibility with the suprailiac and iliac crest region.

The ultrasonic probe holder comprises a ring disposed with respect to the ultrasonic transducer at a predetermined distance of 5 cm. Using an extendable member, the distance between the ring and the ultrasonic probe can be increased to 10 cm. The ring permits the operator to controllably position the ultrasonic probe holder and the ultrasonic transducer with respect to the anterior superior iliac spine. The operator can palpate the anterior superior iliac spine in a subject. The ultrasonic probe holder is then placed so that the ring opening is positioned over the anterior superior iliac spine and the ultrasonic transducer is positioned over the desired region, for example, superiorly towards the subject's head. The undersurface of the ultrasonic probe holder is stabilized against the abdominal wall. The operator will then confirm correct placement of the ultrasonic probe holder by palpating the anterior superior iliac spine again through the ring opening. Once correct placement of the ultrasonic probe holder has been confirmed, the measurement will be obtained. Measurements can be repeated with the transducer pointing medially, laterally, or inferiorly.

Ultrasonic probe holders for the third prototype system are available in different sizes and shapes including curved shapes of different radii in order to achieve a good fit between the ultrasonic probe holder and the abdominal wall in the region of the anterior superior iliac spine and the iliac crest. The basic configuration and all signal processing and data analysis aspects of the ultrasonic probes used in the third prototype ultrasonic system are otherwise similar or identical to that used in the first and second prototype ultrasonic system described above.

All experiments performed on animal subjects (including humans) shall be performed with the highest ethical and medical standards and in accordance with the relevant laws, guidelines and regulations of the relevant governing jurisdiction(s) or professional association(s), including, where appropriate, compliance under 45 CFR 46 relating to United States federal policy for the protection of human subjects.

Example 1

Monitoring of Paraumbilical Adipose Tissue Thickness During a Diet Program

One hundred obese patients are enrolled in a diet program. Patients range in age from 25 to 65 years. Fifty patients are male, the other 50 patients are female. The diet program lasts for a period of 6 months. Ultrasonic measurements of adipose tissue thickness in the paraumbilical region are performed using the first prototype ultrasonic system described in General Materials and Methods with only one ultrasonic probe attached to the ultrasonic probe holder. Ultrasonic measurements of adipose tissue thickness are performed at baseline prior to initiation of the diet program and one week, two weeks, four weeks, 2 months, 3 months, 4 months, 5 months, and 6 months after initiation of the diet program. Ultrasonic measurements of adipose tissue thickness are performed with the ultrasonic probe located superior to the umbilicus.

Measurements obtained at the different time points demonstrate a progressive decrease in adipose tissue layer thickness in those patients who are compliant with the diet program. Patients who are non- or partially compliant with the diet program demonstrate no or a smaller decrease in adipose tissue layer thickness than patients who are compliant with the diet program.

Example 2

Assessment of Paraumbilical Adipose Tissue Distribution During a Diet Program Using a Multi-Probe Device One hundred obese patients are enrolled in a diet program. Patients range in age from 25 to 65 years. Fifty patients are male, the other 50 patients are female. The diet program lasts for a period of 6 months. Ultrasonic measurements of adipose tissue thickness in the paraumbilical region are performed using the second prototype ultrasonic system described in General Materials and Methods with four ultrasonic probes attached to the ultrasonic probe holder. Ultrasonic measurements of adipose tissue thickness are performed at baseline prior to initiation of the diet program and one week, two weeks, four weeks, 2 months, 3 months, 4 months, 5 months, and 6 months after initiation of the diet program. Ultrasonic measurements of adipose tissue thickness are performed superior to the umbilicus, lateral to the right of the umbilicus, lateral to the left of the umbilicus, and inferior to the umbilicus using the four ultrasonic probes attached to the ultrasonic probe holder.

Measurements obtained at the different time points demonstrate a progressive decrease in adipose tissue layer thickness in those patients who are compliant with the diet program. The decrease in adipose tissue layer thickness is similar on the left side and the right side of the umbilicus in all patients compliant with the diet program. However, some patients compliant with the diet program demonstrate an inhomogeneous decrease in adipose tissue layer thickness with a lower decrease in adipose tissue thickness observed inferior to the umbilicus than superior to the umbilicus.

Example 3

Assessment of Paraumbilical Adipose Tissue Distribution During a Diet Program Using a Single Probe Device One hundred obese patients are enrolled in a diet program. Patients range in age from 25 to 65 years. Fifty patients are male, the other 50 patients are female. The diet program lasts for a period of 6 months. Ultrasonic measurements of adipose tissue thickness in the paraumbilical region are performed using the first prototype ultrasonic system described in General Materials and Methods with only one ultrasonic probe attached to the ultrasonic probe holder. Ultrasonic measurements of adipose tissue thickness are performed at baseline prior to initiation of the diet program and one week, two weeks, four weeks, 2 months, 3 months, 4 months, 5 months, and 6 months after initiation of the diet program. An initial ultrasonic measurements of adipose tissue thickness is performed with the ultrasonic probe positioned superior to the umbilicus. The measurement is then repeated with the probe positioned lateral to the right of the umbilicus, then lateral to the left of the umbilicus, and, finally, inferior to the umbilicus.

Measurements obtained at the different time points demonstrate a progressive decrease in adipose tissue layer thickness in those patients who are compliant with the diet program. The decrease in adipose tissue layer thickness is similar on the left side and the right side of the umbilicus in all patients compliant with the diet program. However, some patients compliant with the diet program demonstrate an inhomogeneous decrease in adipose tissue layer thickness with a lower decrease in adipose tissue thickness observed inferior to the umbilicus than superior to the umbilicus similar to the results in Example 2.

Example 4

Monitoring of Muscle Tissue Thickness During an Exercise Program

One hundred moderately obese patients are enrolled in a fitness program. Patients range in age from 30 to 60 years. Fifty patients are male, the other 50 patients are female. The fitness program lasts for a period of 6 months. The patients follow a defined nutritional regimen during the 6-month fitness program. Ultrasonic measurements of adipose tissue thickness and muscle tissue thickness in the paraumbilical region are performed using the first prototype ultrasonic system described in General Materials and Methods with only one ultrasonic probe attached to the ultrasonic probe holder. Ultrasonic measurements of adipose tissue thickness and muscle tissue thickness are performed at baseline prior to initiation of the fitness program and one week, two weeks, four weeks, 2 months, 3 months, 4 months, 5 months, and 6 months after initiation of the fitness program. Ultrasonic measurements of adipose tissue thickness and muscle tissue thickness are performed with the ultrasonic probe located lateral to the right and lateral to the left of the umbilicus. The measured muscle tissue layer includes the rectus abdominis, external oblique, and internal oblique muscles of the abdomen.

Measurements obtained at the different time points demonstrate a progressive decrease in adipose tissue layer thickness and increase in muscle tissue layer thickness in those patients who are compliant with the exercise program and the nutritional regimen. Patients who are non- or partially compliant with the exercise program and the nutritional regimen demonstrate no or a smaller decrease in adipose tissue layer thickness and no or a smaller increase in muscle tissue layer thickness than patients who are compliant with the program.

Example 5

Monitoring of Adipose Tissue Thickness in the Region of the Anterior Superior Iliac Spine and the Iliac Crest During a Diet Program One hundred obese patients are enrolled in a diet program. Patients range in age from 25 to 65 years. Fifty patients are male, the other 50 patients are female. The diet program lasts for a period of 6 months. Ultrasonic measurements of adipose tissue thickness in the region of the anterior superior iliac spine and the iliac crest are performed using the third prototype ultrasonic system described in General Materials and Methods. All measurements are performed with the ring opening positioned over the anterior superior iliac spine and the ultrasonic transducer pointing superiorly towards the subject's head.

Ultrasonic measurements of adipose tissue thickness are performed at baseline prior to initiation of the diet program and one week, two weeks, four weeks, 2 months, 3 months, 4 months, 5 months, and 6 months after initiation of the diet program.

Measurements obtained at the different time points demonstrate a progressive decrease in adipose tissue layer thickness in those patients who are compliant with the diet program. Patients who are non- or partially compliant with the diet program demonstrate no or a smaller decrease in adipose tissue layer thickness than patients who are compliant with the diet program.

PUBLICATIONS

PUBLICATIONS

U.S. PATENT DOCUMENTS

| | | |
|---|---|---|
| 4,043,181 | Aug. 23, 1977 | Nigam, A. K. |
| 4,224,829 | Sep. 30, 1980 | Kawabuchi, M., et al. |
| 4,242,911 | Jan. 6, 1981 | Martin, H. E. |
| 4,388,831 | Jun. 21, 1983 | Sherman, I. N. |
| 4,446,737 | May 8, 1984 | Hottier, F. |
| 4,483,075 | Nov. 20, 1984 | Kundin, J. I. |
| 4,540,946 | Sep. 10, 1985 | Sainz, A. J., et al. |
| 4,658,827 | Dec. 21, 1987 | He, P., et al. |
| 4,688,428 | Aug. 25, 1987 | Nicolas, J.-M. |
| 4,702,258 | Oct. 27, 1987 | Nicolas, J.-M., et al. |
| 4,830,015 | May 16, 1989 | Okazaki, K. |
| 4,833,323 | May 23, 1989 | Scholze, C. |
| 4,947,862 | Aug. 14, 1990 | Kelly, K. A. |
| Des. 320,662 | Oct. 8, 1991 | Nakai, T. |
| 5,208,747 | May 4, 1993 | Wilson, J. |
| 5,216,817 | Jun. 8, 1993 | Misevich, K. W., et al. |
| 5,235,988 | Aug. 17, 1993 | Johnson, D. S., et al. |
| 5,271,403 | Dec. 21, 1993 | Paulos, J. J. |
| 5,303,708 | Apr. 19, 1994 | Stouffer, J. R. |
| 5,316,003 | May 31, 1994 | Stouffer, J. R. |
| 5,353,796 | Oct. 11, 1994 | Schroeder, A. L., et al. |
| 5,617,864 | Apr. 8, 1997 | Stouffer, J. R., et al. |
| PCT/US97/18993 | Filed Oct. 21, 1997 | Lang, P., et al. |

FOREIGN PATENT DOCUMENTS

| | | |
|---|---|---|
| PCT WO 93/12419 | Jun. 24, 1993 | Lake, R. J., et al. |

PUBLICATIONS

OTHER PUBLICATIONS

American College of Sports Medicine, in: "ACSM's guidelines for exercise testing and prescription", eds., pp. 53–63, 1995.
Booth, R. A. D., et al., Br J Nutr, vol. 20, pp. 719–725, 1966.
Brozek, J., et al., Ann NY Acad Sci, vol. 110, pp. 113–140, 1963.
Chumlea, W. C., et al., Am J Phys Anthropol, vol. 71, pp. 351–357, 1986.
Fanelli, M. T., et al., Int J Obesity, vol. 12, pp. 125–132, 1988.
Jackson, A. S., et al., Br J Nutr, vol. 1978, pp. 497–504, 1978.
Jebb, S. A., et al., Am J Clin Nutr, vol. 58, pp. 455–462, 1993.
Jones, P. R. M., et al., Am J Phys Anthropol, vol. 71, pp. 359–363, 1986.
Khati, N. J., et al., Radiographics, vol. 182 (2), pp. 413–431, 1998.
Kuczmarski, R. J., et al., Am J Clin Nutr, vol. 45, pp. 717–724, 1987.
Paijmans, I. J. M., et al., J Am Coll Nutrit, vol. 11, pp. 145–151, 1992.
Ramirez, M. E., Am J Phys Anthropol, vol. 89, pp. 347–357, 1992.
Reali, U., et al., Plast Reconstr Surg, vol. 93, pp. 1050–1055, 1994.
Rolland-Cachera, M. F., Horm Res, vol. 39 (suppl. 3), pp. 25–40, 1993.
Sehgal, C. M., J Acoust Soc Am, vol. 94, pp. 1944–1952, 1993.
Seidell, J. C., et al., Eur J Clin Invest, vol. 18 (3), pp. 243–249, 1988.
Siri, W. E., Univ Calif Donner Lab Med Phys Rep, vol. March, pp. 1956.
Volz, P. A., et al., Med Sci Sports Exerc, vol. 16, pp. 97–102, 1984.
Williams, J. L., J Acoust Soc Am, vol. 91, pp. 1106–1112, 1992.

All documents and publications, including patents and patent application documents, are herein incorporated by reference to the same extent as if each publication were individually incorporated by reference.

We claim:

1. An apparatus for acoustically measuring body fat in an anatomical region of a human body, the apparatus comprising:

a substantially rigid support member designed to contact the anatomical region, the support member having at least a first portion and a second portion in spaced relation with one another and separated from one another by a separation distance;

the first portion geometrically corresponding to an anatomical feature of the anatomical region; and the second portion geometrically corresponding to an acoustical transducer and permitting acoustic signals to pass between the acoustical transducer and the anatomical region.

2. The apparatus of claim 1, wherein the first and second portions of the support member are substantially at opposite ends of the support member.

3. The apparatus of claim 1, wherein the distance between the first and second portions of the support member is fixed.

4. The apparatus of claim 1, wherein the distance between the first and second portions of the support member is variable by way of an adjustable length arm.

5. The apparatus of claim 1, wherein the support member is designed to contact a human abdomen.

6. The apparatus of claim 1, wherein the first portion of the support member geometrically corresponds to a human umbilicus.

7. The apparatus of claim 1, further comprising an acoustical transducer adapted for mechanical coupling to the second portion of the support member.

8. The apparatus of claim 7, wherein the acoustical transducer is an ultrasonic transducer operational in a frequency range greater than 20 kHz.

9. The apparatus of claim 7, wherein the second portion of the support member holds the acoustical transducer at an approximate angular position with respect to a human abdominal wall.

10. The apparatus of claim 9, wherein the angular position is between 60 degrees and 90 degrees (perpendicular).

11. The apparatus of claim 7, wherein the acoustical transducer comprises a transmitting element and a receiving element that respectively transmit and receive acoustical signals.

12. The apparatus of claim 7, wherein the acoustical transducer comprises any one of: a transmitting element that transmits acoustical signals and a receiving element that receives acoustical signals.

13. The apparatus of claim 1, wherein the first portion of the support member comprises an opening, adapted for placement over the anatomical feature, and adapted to allow a practitioner to place his or her finger within the opening to palpate the anatomical feature.

14. The apparatus of claim 1, wherein the first portion of the support member comprises an umbilicus positioning unit adapted to fit within a human umbilicus which forms an anatomical feature landmark from which the second portion of the support member is spatially offset.

15. The apparatus of claim 14, wherein the umbilicus positioning unit includes a substantially cylindrical member with a convex tip adapted for placement in the human umbilicus.

16. The apparatus of claim 14, wherein the umbilicus positioning unit includes a bulb at an end portion thereof for placement in the human umbilicus.

17. The apparatus of claim 1, wherein the support member further comprises a third portion that geometrically corresponds to a second acoustical transducer and permits acoustic signals to pass between the second acoustical transducer and the anatomical region.

18. The apparatus of claim 1, further being coupled to a processor that computes body fat based on the acoustic signals.

19. A method for measuring body fat in an anatomical region of a human body, comprising:

placing a support member on the anatomical region;

selecting an anatomical feature of the anatomical region as a reference point for measuring the body fat;

positioning a first portion of the support member over the anatomical feature of the anatomical region;

positioning an acoustical transducer at a second portion of the support member and in spaced relation with the anatomical feature;

transmitting an acoustic signal from the acoustical transducer into the anatomical region;

receiving a return acoustic signal from the anatomical region; and making an acoustical determination of the body fat content in the vicinity of the acoustical transducer based on the acoustic signals.

20. The method of claim 19, further comprising recording a result of the acoustical determination on a data processing apparatus.

21. The method of claim 19, wherein selecting the anatomical feature comprises using a same anatomical feature previously used in a similar body fat measurement.

22. The method of claim 19, wherein selecting the anatomical feature comprises determining a location in the anatomical region in which the body fat measurement is to be conducted.

23. An apparatus for measuring body fat in an anatomical region of the human body, comprising:

support means for supporting at least an acoustic transducer assembly, the support means having a first portion and a second portion in spaced relation with one another and separated by a separation distance;

positioning means, proximal to the first portion of the support means, for geometrically locating the first portion of the support means with respect to a reference anatomical feature of the anatomical region; and an acoustical transducer assembly, proximal to the second portion of the support means, the acoustical transducer adapted for interrogating tissue in the anatomical region to obtain a signal corresponding to body fat in the anatomical region.

24. A method for providing an adipose tissue control program, comprising:

placing an umbilicus positioning unit in contact with a subject's abdomen, at the subject's umbilicus;

placing an ultrasonic transducer proximal to the subject's abdomen a pre-determined distance away from the umbilicus positioning unit, using the umbilicus positioning unit as a spatial reference point;

transmitting an ultrasonic signal from the transducer into the adipose tissue of the abdomen;

receiving a return ultrasonic signal from the adipose tissue of the abdomen indicative of an amount of adipose tissue in a region of the subject's abdomen;

determining an amount of adipose tissue in the region of the subject's abdomen at least based on the returned ultrasonic signal; and prescribing an adipose tissue control treatment based on the amount of adipose tissue in the region of the subject's abdomen.

25. The method of claim 24, wherein prescribing the treatment includes providing a nutritional regime to control muscle or adipose tissue.

26. The method of claim 24, further comprising computing an amount of body fat based on the ultrasonic signals.

* * * * *